(12) United States Patent
Ide et al.

(10) Patent No.: US 9,494,861 B2
(45) Date of Patent: Nov. 15, 2016

(54) POSITIVE PHOTOSENSITIVE COMPOSITION, THIN FILM TRANSISTOR, AND COMPOUND

(71) Applicant: KANEKA CORPORATION, Osaka (JP)

(72) Inventors: Masahito Ide, Osaka (JP); Hirofumi Inari, Osaka (JP); Aki Kitajima, Osaka (JP); Komei Tahara, Osaka (JP); Takao Manabe, Osaka (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 14/410,438

(22) PCT Filed: Jul. 2, 2013

(86) PCT No.: PCT/JP2013/068097
§ 371 (c)(1),
(2) Date: Dec. 22, 2014

(87) PCT Pub. No.: WO2014/007231
PCT Pub. Date: Jan. 9, 2014

(65) Prior Publication Data
US 2015/0192850 A1    Jul. 9, 2015

(30) Foreign Application Priority Data

| Jul. 4, 2012 | (JP) | 2012-150354 |
| Oct. 18, 2012 | (JP) | 2012-230873 |
| Dec. 13, 2012 | (JP) | 2012-272734 |
| Dec. 26, 2012 | (JP) | 2012-282900 |
| Mar. 26, 2013 | (JP) | 2013-063936 |

(51) Int. Cl.
*G03F 7/004* (2006.01)
*G03F 7/027* (2006.01)
(Continued)

(52) U.S. Cl.
CPC ............. *G03F 7/027* (2013.01); *C07F 7/1852* (2013.01); *C08G 77/388* (2013.01); *C08K 5/549* (2013.01);
(Continued)

(58) Field of Classification Search
CPC .......... G03F 7/004; G03F 7/11; G03F 7/039; G03F 7/075; G03F 7/0757; C08K 5/549; C08G 77/388; H01L 21/021126; H01L 21/02216; H01L 21/3122; H01L 2924/12044; H01L 21/02126; H01L 21/32; H01L 2924/120443
USPC .......... 430/270.1; 556/400; 528/33; 257/347
See application file for complete search history.

(56) References Cited

U.S. PATENT DOCUMENTS

| 2004/0137241 A1 | 7/2004 | Lin et al. |
| 2010/0099790 A1* | 4/2010 | Manabe .................. C07F 7/21 522/172 |

(Continued)

FOREIGN PATENT DOCUMENTS

| EP | 2 236 543 A1 | 10/2010 |
| JP | 2009-203302 | 9/2009 |

(Continued)

OTHER PUBLICATIONS

Tronc et al., "Polycondensation using hydrosilylation: a tool for preparing tailor-made polysiloxanes with anchoring groups", Polymer, 41 (13), pp. 5039-5046, 2000.

(Continued)

*Primary Examiner* — Amanda C Walke
(74) *Attorney, Agent, or Firm* — Hamre, Schumann, Mueller & Larson, P.C.

(57) ABSTRACT

The present invention aims to provide positive photosensitive compositions that have excellent patterning properties and can exhibit excellent electrical insulation reliability when cured (as thin films). The positive photosensitive composition according to a first aspect of the present invention is characterized by including (A) a compound that contains an alkenyl group or a SiH group within a molecule and has a structure that decomposes in the presence of acid to generate an acidic group or a hydroxyl group; (B) a compound that contains a SiH group or an alkenyl group within a molecule; (C) a hydrosilylation catalyst; and (D) a photoacid generator.

26 Claims, 1 Drawing Sheet

(51) Int. Cl.
  *C08K 5/549* (2006.01)
  *C08G 77/388* (2006.01)
  *G03F 7/039* (2006.01)
  *G03F 7/075* (2006.01)
  *G03F 7/40* (2006.01)
  *H01L 51/00* (2006.01)
  *H01L 51/05* (2006.01)
  *C07F 7/18* (2006.01)
  *H01L 21/02* (2006.01)
  *H01L 21/033* (2006.01)

(52) U.S. Cl.
  CPC ........... *G03F 7/0392* (2013.01); *G03F 7/0755* (2013.01); *G03F 7/0757* (2013.01); *G03F 7/40* (2013.01); *H01L 51/0094* (2013.01); *H01L 51/0508* (2013.01); *H01L 21/02126* (2013.01); *H01L 21/02216* (2013.01); *H01L 21/0332* (2013.01)

(56) References Cited

U.S. PATENT DOCUMENTS

| 2011/0001190 A1* | 1/2011 | Ide ................. C08G 77/388 257/347 |
| 2012/0034387 A1 | 2/2012 | Apanius et al. |
| 2013/0131264 A1* | 5/2013 | Nishimiya ............. C08L 83/14 524/588 |

FOREIGN PATENT DOCUMENTS

| JP | 2010-235862 | 10/2010 |
| JP | 2010-285519 | 12/2010 |
| JP | 2011-022173 | 2/2011 |
| JP | 2011-033772 | 2/2011 |
| JP | 2011-227291 | 11/2011 |

OTHER PUBLICATIONS

Tronc et al., "Adsorption of Polysiloxanes Bearing Anchoring Phenol Groups onto Silica Particles", Langmuir, 15 (20), pp. 7080-7083, 1999.

* cited by examiner

POSITIVE PHOTOSENSITIVE COMPOSITION, THIN FILM TRANSISTOR, AND COMPOUND

TECHNICAL FIELD

The present invention relates to positive photosensitive compositions, thin film transistors, and compounds.

BACKGROUND ART

Positive photosensitive compositions are widely used in the manufacture of displays, semiconductors and the like, and positive resists mainly containing acrylic or phenolic resins have been proposed and marketed.

In particular, as positive photosensitive compositions used as permanent resists, whose cured products (thin films) are left as functional films in devices after patterning, positive photosensitive compositions based on more durable resins, such as a polyimide polymer (Patent Literature 1) or a silicon polymer (Patent Literature 2), or other materials have been proposed.

The thin films obtained by curing these positive photosensitive compositions, unfortunately, lack sufficient insulation properties for use as insulating films or the like. Thus, no positive photosensitive compositions whose cured products satisfy the insulation properties required for insulating films have as yet been developed.

CITATION LIST

Patent Literature

Patent Literature 1: JP 2011-033772 A
Patent Literature 2: JP 2011-022173 A

SUMMARY OF INVENTION

Technical Problem

The present invention aims to provide positive photosensitive compositions that have excellent patterning properties and can exhibit excellent electrical insulation reliability when cured (as thin films); and thin film transistors including as insulating films thin films obtained by curing the positive photosensitive compositions.

The present invention also aims to provide compounds that can be suitably used for preparing positive photosensitive compositions that have excellent patterning properties and can exhibit excellent electrical insulation reliability when cured (as thin films).

Solution to Problem

The inventors of the present invention conducted intensive studies and thereby found the following features capable of solving the above problem, and thus completed the present invention.

Specifically, a positive photosensitive composition according to a first aspect of the present invention contains:

(A) a compound that contains an alkenyl group or a SiH group within a molecule and has a structure that decomposes in the presence of acid to generate an acidic group or a hydroxyl group;
(B) a compound that contains a SiH group or an alkenyl group within a molecule;
(C) a hydrosilylation catalyst; and
(D) a photoacid generator.

In the positive photosensitive composition of the first aspect of the present invention, the component (B) is preferably a compound having no structure that decomposes in the presence of acid to generate an acidic group or a hydroxyl group.

In the positive photosensitive composition of the first aspect of the present invention, preferably, the component (A) is a compound that contains a SiH group within a molecule and has a structure that decomposes in the presence of acid to generate an acidic group or a hydroxyl group, and the component (B) is a compound that contains an alkenyl group within a molecule.

In the positive photosensitive composition of the first aspect of the present invention, the structure that decomposes in the presence of acid to generate an acidic group or a hydroxyl group in the component (A) is preferably a phenol structure with protected functionality or a carboxylic acid structure with protected functionality.

In the positive photosensitive composition of the first aspect of the present invention, the phenol structure with protected functionality is preferably a bisphenol structure with protected functionality, and more preferably a bisphenol structure whose functionality is protected by a trialkylsilyl group or a butoxycarbonyl group.

In the positive photosensitive composition of the first aspect of the present invention, the component (A) preferably has a bisphenol structure, more preferably a bisphenol S structure or a bisphenol F structure.

In the positive photosensitive composition of the first aspect of the present invention, the carboxylic acid structure with protected functionality preferably contains an acetal bond or a carboxylic acid tertiary ester bond.

In the positive photosensitive composition of the first aspect of the present invention, the structure containing a carboxylic acid tertiary ester bond is preferably protected by an aliphatic ring structure, more preferably by an adamantane structure.

In the positive photosensitive composition of the first aspect of the present invention, at least one of the component (A) and the component (B) is preferably a siloxane-based compound.

In the positive photosensitive composition of the first aspect of the present invention, it is preferred that of the components (A) and (B), at least the component (A) be a siloxane-based compound, and the component (A) have a cyclic siloxane structure.

In the positive photosensitive composition of the first aspect of the present invention, the siloxane-based compound preferably contains a polyhedral polysiloxane structure formed of 6 to 24 Si atoms.

In the positive photosensitive composition of the first aspect of the present invention, the polyhedral polysiloxane structure is preferably obtained by a hydrosilylation reaction of a SiH group-containing siloxane compound and an alkenyl group-containing polyhedral polysiloxane compound formed of 6 to 24 Si atoms.

In the positive photosensitive composition of the first aspect of the present invention, the polyhedral polysiloxane structure is preferably obtained by a hydrosilylation reaction of a polyhedral polysiloxane compound represented by formula (I) and a cyclic siloxane compound represented by formula (II), the formulas (I) and (II) respectively being:

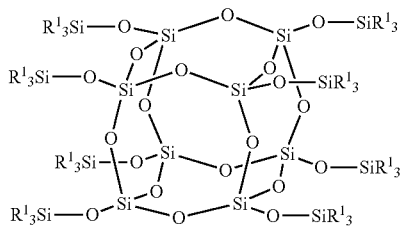
(I)

wherein $R^1$s are each a hydrogen atom or a $C_{1-10}$ organic group, at least one of $R^1$s is a hydrogen atom or an alkenyl group, and $R^1$s may be the same as or different from one another, and

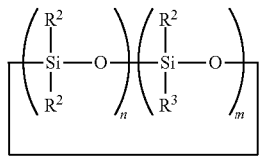
(II)

wherein $R^2$s are each a $C_{1-6}$ organic group and may be the same as or different from one another; $R^3$s are each a hydrogen atom or an alkenyl group and may be the same as or different from one another; n represents an integer of 0 to 10; and m represents an integer of 1 to 10.

In the positive photosensitive composition of the first aspect of the present invention, the component (A) is preferably a compound that decomposes in the presence of acid to become alkali-soluble.

A positive photosensitive composition according to a second aspect of the present invention includes the positive photosensitive composition of the first aspect of the present invention but contains in place of the component (A) and the component (B), (E) a compound obtained by a hydrosilylation reaction of the component (A) and the component (B).

A positive photosensitive composition according to a third aspect of the present invention contains:

(F) a compound that has a bisphenol structure whose phenolic hydroxyl functional groups are protected by a trialkylsilyl group; and (D) a photoacid generator.

In the positive photosensitive composition of the third aspect of the present invention, the bisphenol structure in the component (F) is preferably a bisphenol S structure or a bisphenol F structure.

A positive photosensitive composition according to a fourth aspect of the present invention contains:

(G) a compound having a structure represented by formula (X1) or (X2);

(H) a compound having a structure that decomposes in the presence of acid to generate an acidic group or a hydroxyl group; and (D) a photoacid generator, the formulas (X1) and (X2) respectively being:

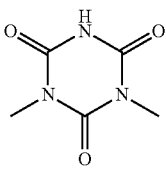
(X1)

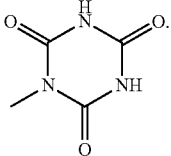
(X2)

In the positive photosensitive compositions of the first to fourth aspects of the present invention, the component (D) is preferably an iodonium salt or a sulfonium salt.

The positive photosensitive compositions of the first to fourth aspects of the present invention preferably further contain (I) an alkali-soluble component.

In the positive photosensitive compositions of the first to fourth aspects of the present invention, the component (I) is preferably a SiH group- or alkenyl group-containing compound.

In the positive photosensitive compositions of the first to fourth aspects of the present invention, the component (I) is preferably a compound having a structure represented by the following formula (X1) or (X2):

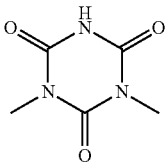
(X1)

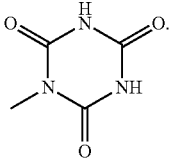
(X2)

The positive photosensitive compositions of the second to fourth aspects of the present invention preferably further contain (J) a compound that contains an alkenyl group and has no structure that decomposes in the presence of acid to generate an acidic group or a hydroxyl group.

The positive photosensitive compositions of the first to fourth aspects of the present invention preferably further contain (K) a sensitizer.

A thin film transistor according to a fifth aspect of the present invention includes as a gate insulator a thin film obtained by curing one of the positive photosensitive compositions of the first to fourth aspects of the present invention.

Moreover, a thin film transistor according to a sixth aspect of the present invention includes as a passivation film a thin film obtained by curing one of the positive photosensitive compositions of the first to fourth aspects of the present invention.

A compound according to a seventh aspect of the present invention relates to a compound represented by the following formula (III):

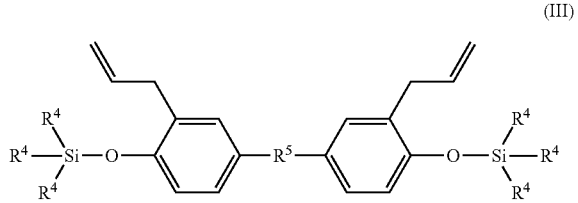

(III)

wherein $R^4$s each represent a $C_{1-6}$ alkyl group having no unsaturated bond, and $R^4$s may be the same as or different from one another; and $R^5$ is any structure that allows the compound to form a bisphenol compound.

Advantageous Effects of Invention

The positive photosensitive compositions of the first to fourth aspects of the present invention have excellent patterning properties and can exhibit excellent electrical insulation reliability when cured (as thin films).

The thin film transistors of the fifth and sixth aspects of the present invention include as a gate insulator or a passivation film a thin film obtained by curing one of the first to fourth positive photosensitive compositions, and thus are excellent in transistor performance and reliability.

The compound of the seventh aspect of the present invention can be suitably used in positive photosensitive compositions that have excellent patterning properties and can exhibit excellent electrical insulation reliability when cured (as thin films).

DESCRIPTION OF EMBODIMENTS

Figure 1:
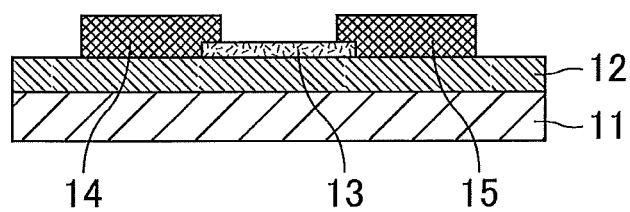
FIG. 1 is a schematic cross sectional view illustrating an example of the thin film transistor of the fifth aspect of the present invention.

<<Positive Photosensitive Composition of the First Aspect of the Present Invention>>

First, the positive photosensitive composition of the first aspect of the present invention will be described.

The positive photosensitive composition of the first aspect of the present invention is characterized by containing:

(A) a compound that contains an alkenyl group or a SiH group within a molecule and has a structure that decomposes in the presence of acid to generate an acidic group or a hydroxyl group;

(B) a compound that contains a SiH group or an alkenyl group within a molecule;

(C) a hydrosilylation catalyst; and (D) a photoacid generator.

<Component (A)>

The component (A) is a compound that contains an alkenyl group or a SiH group within a molecule and has a structure that decomposes in the presence of acid to generate an acidic group or a hydroxyl group. The component (A) is decomposed by an acid generated from the photoacid generator (D) to generate an acidic group or a hydroxyl group, and thereby becomes soluble in developers. Thus, the use of such a component (A) along with the component (D) permits formation of positive patterns.

The structure that decomposes in the presence of acid to generate an acidic group or a hydroxyl group is not particularly limited. For excellent patterning properties and excellent insulation properties when the composition is cured (as a thin film), the structure is preferably a phenol structure with protected functionality or a carboxylic acid structure with protected functionality.

The phenol structure with protected functionality herein means a phenol structure in which the hydrogen atom(s) of the hydroxyl group(s) is replaced with a compound residue.

In view of being more significantly favorable to the effect of providing excellent patterning properties and excellent insulation properties when the composition is cured (as a thin film), the phenol structure with protected functionality is preferably a bisphenol structure with protected functionality, and more preferably a bisphenol structure whose functionality is protected by a trialkylsilyl group or a butoxycarbonyl group.

Moreover, the compound residue is preferably a $C_{1-50}$ organic group or an organic silicon group.

The bisphenol structure with protected functionality which contains a $C_{1-50}$ organic group or an organic silicon group as the compound residue is represented by the following formula (IV).

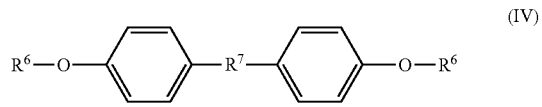

(IV)

In the formula (IV), $R^6$s each represent a $C_{1-50}$ organic group or an organic silicon group; $R^7$ is any structure that allows the structure to form a bisphenol structure; and the hydrogen atoms on the aromatic rings may be substituted.

A compound having the phenol structure with protected functionality (especially, a bisphenol structure with protected functionality represented by the formula (IV)) may be obtained, for example, by a method of using a compound highly reactive with active hydrogen or by a method including protection by a tert-butoxycarbonyl group in the presence of a Boc reagent.

For efficient production of the target compound, a solvent and/or a catalyst may optionally be used in these methods.

If the component (A) contains a hydrosilylation reactive group such as a SiH group, the method of using a compound highly reactive with active hydrogen is preferred in terms of stability.

Examples of the compounds highly reactive with active hydrogen include halides, carboxylic acids, and silylation agents.

For easy deprotection with the photoacid generator (D), the method of using a compound highly reactive with active hydrogen is preferably a method of protecting a functional group by a trialkylsilyl group using a silylation agent.

The alkyl groups contained in the trialkylsilyl group are not particularly limited. For easy deprotection with the photoacid generator (D), they are each preferably a $C_{1-6}$ alkyl group having no unsaturated bond, and more preferably a methyl group.

The silylation agent used in protecting a functional group by a trialkylsilyl group may be a generally used silylation agent, and specific examples thereof include hexamethyldisilazane, trimethylchlorosilane, tert-butyldimethylchlorosilane, bis(trimethylsilyl)acetamide, bis(trimethylsilyl)trifluoroacetamide, N-methyltrimethylsilylacetamide, N-methyltrimethylsilyltrifluoroacetamide, trimethylsilylimidazole, N,N'-bis(trimethylsilylurea), triethylchlorosilane, triisopropylchlorosilane, and triethylsilane. From the viewpoint of industrial production at low cost, hexamethyldisilazane, trimethylchlorosilane, and tert-butyldimethylchlorosilane are preferred among these silylation agents.

These silylation agents may be used alone or in combination of two or more.

The carboxylic acid structure with protected functionality herein means a carboxylic acid structure in which the hydrogen atom(s) of the carboxyl group(s) is replaced with a compound residue.

In view of being more significantly favorable to the effect of providing excellent patterning properties and excellent insulation properties when the composition is cured (as a thin film), the carboxylic acid structure with protected functionality preferably contains an acetal bond or a carboxylic acid tertiary ester bond.

Examples of the component (A) having the structure containing an acetal bond include diallyl acetal, pentanal diallyl acetal, benzaldehyde diallyl acetal, 1,1,2,2-tetraallyloxyethane, 1,1,2,2-tetraallyloxypropane, 2,2-diallyl-1,3-dioxolane, methoxy methyl acrylate, ethoxy methyl acrylate, 4-vinyl methoxy methyl benzoate, and 4-vinyl ethoxy methyl benzoate.

Alternatively, the component (A) having the structure containing an acetal bond may be previously subjected to a hydrosilylation reaction with a SiH group-containing siloxane compound, and the resulting compound may be used.

In the structure containing a carboxylic acid tertiary ester structure, the carboxylic acid tertiary ester structure may be, for example, a structure in which the carboxyl group is protected by a p-tert-butoxy group, a p-tert-butoxycarbonyl group or the like. The tertiary ester structure is not particularly limited and may be a known one such as a t-butyl ester.

The component (A) that contains an alkenyl group and the structure containing a carboxylic acid tertiary ester structure is not particularly limited, and examples thereof include t-butyl acrylate, t-butyl methacrylate, t-butyl 3-butenoate, 2-methyl 2-adamantyl acrylate, 2-ethyl 2-adamantyl acrylate, 2-methyl 2-adamantyl methacrylate, 2-ethyl 2-adamantyl methacrylate, 1,3-adamantanediol diacrylate, and 1,3-adamantanediol dimethacrylate. For particularly excellent heat resistance, preferred among these are compounds having two or more (meth)acrylic groups, preferably 1,3-adamantanediol diacrylate or 1,3-adamantanediol dimethacrylate.

Alternatively, the component (A) that contains an alkenyl group and the structure containing a carboxylic acid tertiary ester structure may be previously subjected to a hydrosilylation reaction with a SiH group-containing siloxane compound, and the resulting compound may be used.

For excellent contrast in development and excellent heat resistance and insulation properties when the composition is cured as a thin film, the structure containing a carboxylic acid tertiary ester bond is preferably a carboxylic acid tertiary ester structure protected by an aliphatic ring structure. In this case, the tertiary carbon atom protecting the carboxyl group in the carboxylic acid tertiary ester structure may be a carbon atom forming the aliphatic ring structure or a carbon atom present independently without forming the aliphatic ring structure.

In view of contrast in development and exposure sensitivity, the aliphatic ring structure is preferably an adamantane structure.

In the positive photosensitive composition of the first aspect of the present invention, the content of the structure that decomposes in the presence of acid to generate an acidic group or a hydroxyl group in the component (A) is preferably 0.05 to 10 mmol/g, more preferably 0.1 to 5 mmol/g, and still more preferably 0.15 to 3 mmol/g, as determined by $^1$H-NMR using dibromoethane as a standard and expressed in equivalents relative to the combined amount of the component (A) and the component (B).

The component (A) is a compound that contains an alkenyl group or a SiH group within a molecule and has the structure that decomposes in the presence of acid to generate an acidic group or a hydroxyl group.

Alternatively, the component (A) may be the later-mentioned component (E) (a reaction product of a hydrosilylation reaction of the component (A) and the component (B)). In particular, the component (A) may be a compound that contains an alkenyl group and a SiH group and has a structure that decomposes in the presence of acid to generate an acidic group or a hydroxyl group, obtained previously by a hydrosilylation reaction of the component (A) and the component (B).

In view of availability and easy deprotection with the photoacid generator, the component (A) containing an alkenyl group is preferably a compound represented by the formula (III) below or a compound obtained by reacting this compound and the later-mentioned component (B).

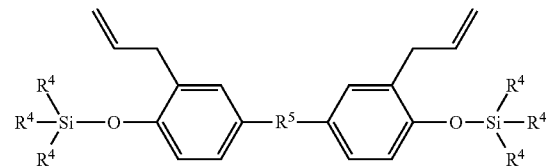

(III)

In the formula (III), $R^4$s each represent a $C_{1-6}$ alkyl group having no unsaturated bond, and $R^4$s may be the same as or different from one another; and $R^5$ is any structure that allows the compound to form a bisphenol structure.

If the component (A) contains an alkenyl group, it preferably has two or more alkenyl groups within a molecule of the component (A), in view of increasing crosslink density and thereby forming a tougher thin film.

The component (A) containing a SiH group may be, for example, a compound obtained by a hydrosilylation reaction of the component (A) containing an alkenyl group and a compound having two or more SiH groups within a molecule.

The compound having two or more SIR groups within a molecule is not particularly limited, and examples thereof include dimethylhydrosilyl group-end-capped siloxanes, cyclic siloxanes containing SIR groups at side chains, acyclic siloxanes, and cage-like siloxanes.

In view of forming a thin film particularly excellent in insulation properties, cyclic siloxane compounds containing SiH groups at side chains are preferred among these.

Examples of the cyclic siloxane compounds containing SiH groups at side chains include 1,3,5,7-tetrahydrogen-1,3,5,7-tetramethylcyclotetrasiloxane, 1-methyl-3,5,7-trihydrogen-1,3,5,7-tetramethyl -cyclotetrasiloxane, 1,3-dimethyl-5,7-dihydrogen-1,3,5,7-tetramethylcyclotetrasiloxane, 1-propyl-3,5,7-trihydrogen-1,3,5,7-tetramethylcyclotetrasiloxane, 1,3-dipropyl-5,7-dihydrogen-1,3,5,7-tetramethyl -cyclotetrasiloxane, 1,3,5-trihydrogen-7-hexyl-1,3,5,7-tetramethylcyclotetrasiloxane, 1,5-dihydrogen-3,7-dihexyl-1,3,5,7-tetramethylcyclotetrasiloxane, 1,3,5-trihydrogen-trimethylcyclosiloxane, 1,3,5,7,9-pentahydrogen-1,3,5,7,9-pentamethylcyclosiloxane, and 1,3,5,7,9,11-hexahydrogen-1,3,5,7,9,11-hexamethylcyclosiloxane. Particularly in view of availability, 1,3,5,7-tetrahydrogen-1,3,5,7-tetramethylcyclotetrasiloxane is preferred among these. These compounds may be used alone or in combination of two or more.

The catalyst used in the hydrosilylation reaction is, not particularly limited and may be a known hydrosilylation catalyst. From the standpoint of catalytic activity, it is preferably chloroplatinic acid, a platinum-olefin complex, a platinum-vinylsiloxane complex or the like.

These hydrosilylation catalysts may be used alone or in combination of two or more.

In the case where the component (A) contains a SiH group, the SiH group content is preferably 0.01 to 15 mmol, more preferably 0.05 to 10 mmol, still more preferably 0.1 to 8 mmol, and particularly preferably 1 to 8 mmol, per gram of the component (A). If the SiH group content is less than 0.01 mmol, insulation properties may be reduced. If the SiH group content is more than 15 mmol, the component (A) may have reduced storage stability.

The component (A) preferably contains a bisphenol structure because the resulting thin film can be improved in chemical resistance, insulation properties, and the like.

Examples of the bisphenol structures include a bisphenol A structure, bisphenol AP structure, bisphenol AF structure, bisphenol B structure, bisphenol BP structure, bisphenol E structure, bisphenol M structure, bisphenol F structure, bisphenol S structure, bisphenol PH structure, bisphenol C structure, bisphenol G structure, bisphenol TMC structure, and bisphenol Z structure.

In view of providing excellent solubility in alkaline developers and thereby forming patterns providing an excellent contrast, preferred among these are a bisphenol A structure, bisphenol B structure, bisphenol C structure, bisphenol E structure, bisphenol F structure, bisphenol AF structure, bisphenol S structure, bisphenol AP structure, and bisphenol PH structure. Particularly in view of availability, also preferred are a bisphenol A structure and a bisphenol S structure. In view of easy deprotection with the photoacid generator, preferred are a bisphenol S structure and a bisphenol F structure.

In the positive photosensitive composition of the first aspect of the present invention, the component (A) may be used alone or in combination of two or more.

In view of patterning properties and the insulation properties of the resulting cured product (thin film), the amount of the component (A) in the positive photosensitive composition of the first aspect of the present invention is preferably 5 to 95 parts by weight, more preferably 10 to 90 parts by weight, and still more preferably 20 to 80 parts by weight, per 100 parts by weight of all the components in the positive photosensitive composition excluding solvent.

The component (A) is preferably a compound that decomposes in the presence of acid to become alkali-soluble. This is because the component (A) decomposes in the presence of acid to become alkali-soluble and thereby makes the positive photosensitive composition of the first aspect of the present invention alkali-soluble, which permits generally used alkaline developers to be used in forming a thin film by curing the positive photosensitive composition of the first aspect of the present invention.

<Component (B)>

The component (B) is a compound that contains a SiH group or an alkenyl group within a molecule.

The component (B) is not particularly limited and may be a known compound. If the component (A) is an alkenyl group-containing compound, the component (B) needs to be a SiH group-containing compound. If the component (A) is a SiH group-containing compound, the component (B) needs to be an alkenyl group-containing compound.

Moreover, the component (B) may or may not have a structure that decomposes in the presence of acid to generate an acidic group or a hydroxyl group.

Alternatively, the component (B) may be the later-mentioned component (E) (a reaction product of a hydrosilylation reaction of the component (A) and the component (B)). In particular, the component (B) may be a compound that contains an alkenyl group and a SiH group and has a structure that decomposes in the presence of acid to generate an acidic group or a hydroxyl group, obtained previously by a hydrosilylation reaction of the component (A) and the component (B).

The component (B) containing an alkenyl group may be, for example, an alkenyl group-containing organic compound or an alkenyl group-containing siloxane compound. Specific examples thereof include diallyl phthalate, triallyl trimellitate, diethylene glycol bisallyl carbonate, trimethylolpropane diallyl ether, trimethylolpropane triallyl ether, pentaerythritol triallyl ether, pentaerythritol tetraallyl ether, 1,1,2,2-tetraallyloxyethane, diallylidene pentaerythritol, triallyl cyanurate, 1,2,4-trivinylcyclohexane, 1,4-butanediol diallyl ether, nonanediol diallyl ether, 1,4-cyclohexane dimethanol diallyl ether, triethylene glycol diallyl ether, trimethylolpropane trivinyl ether, pentaerythritol tetravinyl ether, bisphenol S diallyl ether, divinylbenzene, divinylbiphenyl, 1,3-diisopropenylbenzene, 1,4-diisopropenylbenzene, 1,3-bis(allyloxy)adamantane, 1,3-bis(vinyloxy)adamantane, 1,3,5-tris(allyloxy)adamantane, 1,3,5-tris(vinyloxy)adamantane, dicyclopentadiene, cyclopentadiene, cyclohexadiene, cyclooctadiene, tricyclopentadiene, norbornadiene, vinylnorbornene, vinylcyclohexene, vinylcyclopentene, butadiene, isoprene, octadiene, 1,5-hexadiene, 1,9-decadiene, diallyl ether, bisphenol A diallyl ether, 2,5-diallyl phenol allyl ether, triallyl isocyanurate, diallyl isocyanurate, diallyl monoglycidyl isocyanurate, diallyl monobenzyl isocyanurate, diallyl monopropyl isocyanurate, monoallyl dibenzyl isocyanurate, diallyl monomethyl isocyanurate, monoallyl dimethyl isocyanurate, and polysiloxane compounds containing a vinyl group bonded to a silicon group (i.e., Si—CH═CH$_2$ group).

Examples of the polysiloxane compounds containing a vinyl group bonded to a silicon group include 1,3,5,7-tetravinyl-1,3,5,7-tetramethylcyclotetrasiloxane, 1-propyl-3,5,7-trivinyl-1,3,5,7-tetramethyl -cyclotetrasiloxane, 1,5-divinyl-3,7-dihexyl-1,3,5,7-tetramethylcyclotetrasiloxane, 1,3,5-trivinyl-trimethylcyclosiloxane, 1,3,5,7,9-pentavinyl-1,3,5,7,9-pentamethylcyclosiloxane, and 1,3,5,7,9,11-hexavinyl-1,3,5,7,9,11-hexamethylcyclosiloxane.

The alkenyl group-containing compounds mentioned in the description of the component (A) may be used as the component (B), depending on the combination with the component (A).

In view of forming a cured product (thin film) excellent in transparency, heat resistance, light resistance, and insulation properties, the component (B) is preferably a compound containing an alkenyl group and a structure represented by the following formula (V).

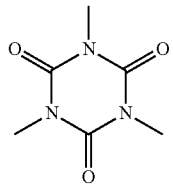

(V)

Examples of the compounds containing an alkenyl group and a structure represented by the formula (V) include triallyl isocyanurate, diallyl isocyanurate, diallyl monoglycidyl isocyanurate, diallyl monobenzyl isocyanurate, diallyl monopropyl isocyanurate, monoallyl dibenzyl isocyanurate, diallyl monomethyl isocyanurate, and monoallyl dimethyl isocyanurate. In view of availability, triallylisocyanurate, diallyl isocyanurate, and diallyl monomethyl isocyanurate are preferred among these.

In view of transparency and curability of the resulting cured product, the component (B) is also preferably an alkenyl group-containing siloxane compound.

In view of availability of the compound, the alkenyl group-containing siloxane compound is preferably a siloxane compound having two or more vinyl groups each bonded to a silicon group (Si—CH=$CH_2$ groups), and more preferably a siloxane compound having 2 to 6 vinyl groups each bonded to a silicon group.

Examples of the siloxane compounds having two or more vinyl groups each bonded to a silicon group (Si—CH=$CH_2$ groups) include 1,3,5,7-tetravinyl-1,3,5,7-tetramethylcyclotetrasiloxane, 1-propyl-3,5,7-trivinyl-1,3,5,7-tetramethyl -cyclotetrasiloxane, 1,5-divinyl-3,7-dihexyl-1,3,5,7-tetramethylcyclotetrasiloxane, 1,3,5-trivinyl-trimethylcyclosiloxane, 1,3,5,7,9-pentavinyl-1,3,5,7,9-pentamethylcyclosiloxane, and 1,3,5,7,9,11-hexavinyl-1,3,5,7,9,11-hexamethylcyclosiloxane.

If the component (B) contains an alkenyl group, it preferably has two or more alkenyl groups within a molecule of the component (B), in view of increasing crosslink density and thereby forming a tougher thin film.

The component (B) containing a SiH group may be, for example, any of the compounds having two or more SiH groups within a molecule as mentioned in the description of the component (A).

In view of forming a tough thin film, the component (B) is preferably an oligomer obtained previously by a partial reaction between polysiloxane compounds or between an organic compound and a polysiloxane compound.

The partial reaction is not particularly limited, but is preferably a hydrosilylation reaction because an electrically and thermally stable C—Si bond is formed by the reaction, as compared with hydrolytic condensation, and the reaction is easily controllable and thus less likely to leave uncrosslinked groups. The monomers used in the partial reaction are not particularly limited and may be an appropriate combination of a SiH group-containing polysiloxane compound with an alkenyl group-containing polysiloxane compound or an organic compound.

If the component (B) contains a SiH group, the SiH group content is preferably 0.01 to 15 mmol, more preferably 0.05 to 10 mmol, still more preferably 0.1 to 8 mmol, and particularly preferably 1 to 8 mmol, per gram of the component (B). If the SiH group content is less than 0.01 mmol, the resulting cured product (thin film) may have reduced insulation properties. If the SiH group content is more than 15 mmol, the component (B) may have reduced storage stability.

Assuming that X and Y represent the amount of SiH groups and the amount of alkenyl groups, respectively, in the component (A) and/or the component (B), the ratio X/Y is preferably 0.2≤X/Y≤5.0. In view of forming a tough thin film, the ratio X/Y is more preferably 0.3≤X/Y≤3.0.

In the positive photosensitive composition of the first aspect of the present invention, the component (B) may be used alone or in combination of two or more.

In the positive photosensitive composition of the first aspect, of the present invention, it is preferred that the component (A) be a compound that contains a SiH group within a molecule and has a structure that decomposes in the presence of acid to generate an acidic group or a hydroxyl group while the component (B) is a compound that contains an alkenyl group within a molecule. This is because the resulting cured product (thin film) has excellent insulation properties.

In the positive photosensitive composition of the first aspect of the present invention, at least one of the component (A) and the component (B) is preferably a siloxane-based compound. More preferably, of the components (A) and (B), at least the component (A) is a siloxane-based compound, and the component (A) has a cyclic siloxane structure. This is because the resulting cured product (thin film) has excellent heat resistance.

Moreover, if at least one of the component (A) and the component (B) is a siloxane-based compound in the positive photosensitive composition of the first aspect of the present invention, the siloxane-based compound preferably contains a polyhedral polysiloxane structure formed of 6 to 24 Si atoms because the resulting cured product (thin film) is excellent in heat resistance, insulation properties and the like. The following is a detailed description of the polyhedral polysiloxane structure formed of 6 to 24 Si atoms.

(Polyhedral Polysiloxane Structure) The polyhedral polysiloxane structure formed of 6 to 24 Si atoms may be, for example, a polyhedral polysiloxane structure represented by the following formula (VI) (here, a polyhedral polysiloxane structure formed of eight Si atoms is given as a representative example).

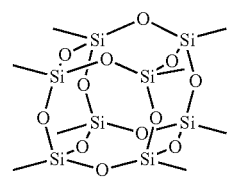

(VI)

The polyhedral polysiloxane structure formed of 6 to 24 Si atoms may be obtained for example by a method of causing a hydrolytic condensation reaction of a silane compound represented by the formula $RSiX_3$ where R represents a group corresponding to the group bonded to the silicon atom in the polyhedral polysiloxane structure formed of 6 to 24 Si atoms; and X represents a hydrolyzable functional group such as a halogen atom or an alkoxy group; or by a method of causing a hydrolytic condensation reaction of the compound of the formula $RSiX_3$ to synthesize a trisilanol compound that has three silanol groups within a molecule, and then reacting the resulting compound with the same or a different trifunctional silane compound to close the ring.

The polyhedral polysiloxane structure formed of 6 to 24 Si atoms is preferably obtained by a hydrosilylation reaction of a SiH group-containing siloxane compound and an alkenyl group-containing polyhedral polysiloxane compound formed of 6 to 24 Si atoms, because such a structure provides high compatibility with other components and thereby allows the formation of an even transparent film.

Examples of the SiH group-containing siloxane compounds include acyclic siloxanes and cyclic siloxanes. Specific examples thereof include the compounds having two or more SiH groups within a molecule (excluding cage-like siloxanes) mentioned in the description of the component (A). Mesh-like siloxanes may also be used. Preferred among these are cyclic siloxanes having two or more SiH groups within a molecule because they allow the formation of a tough film excellent in heat resistance.

The polyhedral polysiloxane structure formed of 6 to 24 Si atoms is preferably a polysiloxane structure typically represented by the formula (VII) below (here, a polyhedral polysiloxane structure formed of eight Si atoms is given as a representative example). In the polysiloxane structure typically represented by the formula (VII), each Si atom at each apex of the polyhedral structure and at least one group containing a SiH group or an alkenyl group are bonded by a siloxane bond. Thus, in the case where at least one of the component (A) and the component (B) in the positive photosensitive composition of the first aspect of the present invention is a siloxane-based compound, the use of a compound having the polysiloxane structure typically represented by the formula (VII) as the siloxane-based compound allows the formation of a tough film.

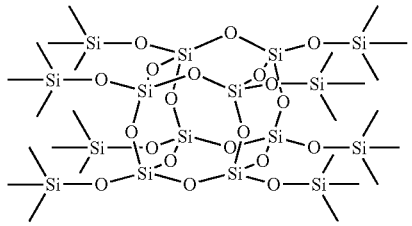

(VII)

The compound having the polysiloxane structure typically represented by the formula (VII) may be synthesized by any known method, such as, for example, by subjecting a tetraalkoxysilane to hydrolytic condensation in the presence of a base such as a quaternary ammonium hydroxide, and reacting the product with a silylation agent such as an alkenyl group-containing silyl chloride. In this synthesis method, the hydrolytic condensation reaction of a tetraalkoxysilane produces a polyhedral polysiloxane compound, and this polysiloxane compound can then be reacted with a silylation agent such as an alkenyl group-containing silyl chloride to provide a polysiloxane compound in which an alkenyl group-containing silyl group is bonded to each Si atom at each apex of the polyhedral structure by a siloxane bond.

Silica or silica-containing materials such as rice hulls may also be used in place of the tetraalkoxysilane to provide a similar polyhedral polysiloxane compound.

Examples of the tetraalkoxysilanes include tetraethoxysilane, tetramethoxysilane, and tetrabutoxysilane. These tetraalkoxysilanes may be used alone or in combination of two or more.

Examples of the quaternary ammonium hydroxides include 2-hydroxyethyl trimethylammonium hydroxide and tetramethylammonium hydroxide. These quaternary ammonium hydroxides may be used alone or in combination of two or more.

The polyhedral polysiloxane structure formed of 6 to 24 Si atoms is preferably obtained by a hydrosilylation reaction of a polyhedral polysiloxane compound represented by the following formula (I) and a cyclic siloxane compound represented by the following formula (II):

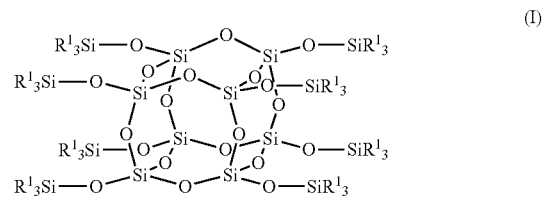

wherein $R^1$s are each a hydrogen atom or a $C_{1-10}$ organic group, at least one of $R^1$s is a hydrogen atom or an alkenyl group, and $R^1$s may be the same as or different from one another,

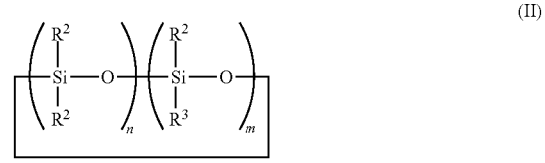

wherein $R^2$s are each a $C_{1-6}$ organic group and may be the same as or different from one another; $R^3$s are each a hydrogen atom or an alkenyl group and may be the same as or different from one another; n represents a number of 0 to 10; and m represents a number of 1 to 10, because such a structure allows the formation of a tough film excellent in heat resistance.

If the polyhedral polysiloxane compound represented by the formula (I) is an alkenyl group-containing compound, the cyclic siloxane compound represented by the formula (II) needs to be a SiH group-containing compound. If the polyhedral polysiloxane compound represented by the formula (I) is a SiH group-containing compound, the cyclic siloxane compound represented by the formula (II) needs to be an alkenyl group-containing compound.

If the polyhedral polysiloxane structure formed of 6 to 24 Si atoms is a polysiloxane structure represented by the formula (VI), the amount of the polysiloxane structure is preferably 2 to 40% by weight, more preferably 3 to 30% by weight, still more preferably 4 to 20% by weight, and particularly preferably 4 to 10% by weight, per 100 parts by weight of all the components in the positive photosensitive composition excluding solvent. When the amount of the polysiloxane structure falls within the range mentioned above, a tough insulating film that has excellent heat resistance, a low dielectric constant, a small leakage current, and good electrical insulation properties can be formed.

<Component (C)>

The component (C) is a hydrosilylation catalyst.

The component (C) may be any known hydrosilylation catalyst. From the standpoint of catalytic activity, it is preferably chloroplatinic acid, a platinum-olefin complex, a platinum-vinylsiloxane complex or the like.

In the positive photosensitive compositions of the first and second aspects of the present invention, the component (C) may be used alone or in combination of two or more.

The amount of the component (C) is preferably 0.01 to 5 mmol, and more preferably 0.02 to 5 mmol, per mole of alkenyl group in the positive photosensitive composition of the first aspect of the present invention. When the amount of the component (C) falls within the range mentioned above, the positive photosensitive composition of the first aspect of the present invention can be cured in a short time and the resulting cured product can be improved in heat resistance and light resistance.

<Component (D)>

The component (D) is a photoacid generator. In the positive photosensitive composition of the first aspect of the present invention, the component (D) generates an acid by exposure to light, and the acid decomposes the component (A) to cause generation of an acidic group or a hydroxyl group, which permits the positive photosensitive composition to become soluble in developers; therefore, positive patterns can be formed.

The component (D) may be any known one that generates a Lewis acid by exposure to light. Preferred are aryl sulfonium salts, aromatic sulfonium or iodonium salts of halogen-containing complex ions, and aromatic onium salts of elements of group II, V, or VI.

In particular, iodonium salts are preferred in view of preparing a positive photosensitive composition that is highly sensitive to a small amount of light exposure, and sulfonium salts are preferred from the standpoint of storage stability of the positive photosensitive composition.

The anion contained in the component (D) is not particularly limited and examples thereof include B $(C_6F_5)_4^-$, $PF_6^-$, $SbF_6^-$, and $CF_3SO_3^-$.

The component (D) may be a commercial product and specific examples thereof include FX-512 (from 3M); UVR-6990 and UVR-6974 (both from Union Carbide); UVE-1014 and UVE-1016 (both from General Electric); KI-85 (from Degussa); SP-152 and SP-172 (both from ADEKA CORPORATION); San-Aid SI-60L, SI-80L, and SI-100L (all from SANSHIN CHEMICAL INDUSTRY CO., LTD.); WPI113 and WPI116 (both from Wako Pure Chemical Industries, Ltd.); RHODORSIL PI2074 (from Rhodia); and BBI-102, BBI-103, BBI-105, TPS-102, TPS-103, TPS-105, MDS-103, MDS-105, DTS-102, DTS-103, and DTS-105 (all from Midori Kagaku Co., Ltd.).

In the positive photosensitive compositions of the first to fourth aspects of the present invention, the component (D) may be used alone or in combination of two or more.

The amount of the component (D) is not particularly limited, but is preferably 0.01 to 10 parts by weight, and more preferably 0.1 to 5 parts by weight, per 100 parts by weight of the total amount of each of the positive photosensitive compositions of the first to fourth aspects of the present invention excluding solvent. When the amount of the component (D) falls within the range mentioned above, patterning properties and the heat resistance and light resistance of the cured product can be improved.

<<Positive Photosensitive Composition of the Second Aspect of the Present Invention>>

Next, the positive photosensitive composition of the second aspect of the present invention will be described.

The positive photosensitive composition of the second aspect of the present invention includes the positive photosensitive composition of the first aspect of the present invention but characteristically contains in place of the component (A) and the component (B), (E) a compound obtained by a hydrosilylation reaction of the component (A) and the component (B).

<Component (E)>

The component (E) is a compound obtained by a hydrosilylation reaction of the component (A) and the component (B).

The component (E) is decomposed by an acid generated from the photoacid generator (D) to generate an acidic group or a hydroxyl group, and thereby becomes soluble in developers. Thus, the use of such a component (E) along with the component (D) permits formation of positive patterns.

In the positive photosensitive composition of the second aspect of the present invention, the components (A) and (B) used for preparing the component (E) are respectively the same as the components (A) and (B) used in the positive photosensitive composition of the first aspect of the present invention.

The component (C) used in the positive photosensitive composition of the first aspect of the present invention may optionally be used in the hydrosilylation reaction of the component (A) and the component (B) to prepare the component (E).

In the positive photosensitive composition of the second aspect of the present invention, the component (E) may be used alone or in combination of two or more.

The components (C) and (D) used in the positive photosensitive composition of the second aspect of the present invention are respectively the same as the components (C) and (D) used in the positive photosensitive composition of the first aspect of the present invention.

<<Positive Photosensitive Composition of the Third Aspect of the Present Invention>>

Next, the positive photosensitive composition of the third aspect of the present invention will be described.

The positive photosensitive composition of the third aspect of the present invention is characterized by containing:

(F) a compound that has a bisphenol structure whose phenolic hydroxyl functional groups are protected by a trialkylsilyl group; and (D) a photoacid generator.

<Component (F)>

The component (F) is a compound that contains a bisphenol structure whose phenolic hydroxyl functional groups are protected by a trialkylsilyl group. The component (F) is deprotected at the trialkylsilyl group with an acid generated from the photoacid generator (D) to generate an acidic group or a hydroxyl group, and thereby becomes soluble in alkali. Thus, the use of such a component (F) along with the component (D) permits formation of positive patterns.

The bisphenol structure is not particularly limited and may be any of the bisphenol structures mentioned for the component (A) in the positive photosensitive composition of the first aspect of the present invention.

In view of providing excellent solubility in alkaline developers and thereby forming patterns providing an excellent contrast, preferred among these are a bisphenol A structure, bisphenol B structure, bisphenol C structure, bisphenol E structure, bisphenol F structure, bisphenol AF structure, bisphenol S structure, bisphenol AP structure, and bisphenol PH structure. Particularly in view of availability, also preferred are a bisphenol A structure and a bisphenol S structure. In view of easy deprotection with the photoacid generator, preferred are a bisphenol S structure and a bisphenol F structure.

The alkyl groups contained in the trialkylsilyl group are not particularly limited. For easy deprotection with the photoacid generator (D), they are each preferably a $C_{1-6}$ alkyl group having no unsaturated bond, and more preferably a methyl group.

The phenolic hydroxyl functional groups may be protected by a trialkylsilyl group by the method of protecting a functional group by a trialkylsilyl group using a silylation agent as mentioned for the component (A) in the positive photosensitive composition of the first aspect of the present invention.

The component (F) may contain a siloxane structure. Containing a siloxane structure leads to easy formation of a cured product (thin film) with high transparency, heat resistance, and light resistance.

The siloxane structure is not particularly limited, and examples thereof include acyclic siloxanes, cyclic siloxanes, mesh-like siloxanes, and cage-like siloxanes.

The component (F) may contain a reactive functional group that allows curing by post-baking. Containing a reactive functional group that allows curing by post-baking leads to easy formation of a tougher cured product (thin film) with high insulation properties.

Examples of the reactive functional groups allowing curing by post-baking include epoxy, acrylic, oxetanyl, alkenyl, SiH, and alkoxysilyl groups. In particular, in view of forming a cured product (thin film) with high transparency, heat resistance, and light resistance, the component (F) preferably contains a SiH group and/or an alkenyl group.

In the component (F), the content of the bisphenol structure whose phenolic hydroxyl functional groups are protected by a trialkylsilyl group is preferably 0.01 to 10 mmol, more preferably 0.05 to 8 mmol, and still more preferably 0.1 to 5 mmol, per gram of the component (F). When the bisphenol structure is contained in the range mentioned above, a tough cured product (thin film) with good alkaline developability can be formed.

In the positive photosensitive composition of the third aspect of the present invention, the component (F) may be used alone or in combination of two or more.

The component (D) used in the positive photosensitive composition of the third aspect of the present invention is the same as the component (D) used in the positive photosensitive composition of the first aspect of the present invention.

The positive photosensitive composition of the third aspect of the present invention may contain a hydrosilylation catalyst. Particularly in the case where hydrosilylation curing is carried out during post-baking, the positive photosensitive composition preferably contains a hydrosilylation catalyst.

The hydrosilylation catalyst is the same as the component (C) used in the positive photosensitive composition of the first aspect of the present invention.

<<Positive Photosensitive Composition of the Fourth Aspect of the Present Invention>>

Next, the positive photosensitive composition of the fourth aspect of the present invention will be described.

The positive photosensitive composition of the fourth aspect of the present invention is characterized by containing:

(G) a compound having a structure represented by the formula (X1) or (X2) below;
(H) a compound having a structure that decomposes in the presence of acid to generate an acidic group or a hydroxyl group; and
(D) a photoacid generator.

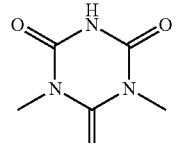

(X1)

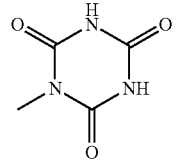

(X2)

<Component (G)>

The component (G) is a compound having a structure represented by the formula (X1) or (X2).

The component (G) is not particularly limited, and examples thereof include diallyl isocyanuric acid and monoallyl isocyanuric acid.

In the positive photosensitive composition of the fourth aspect of the present invention, the component (G) may be used alone or in combination of two or more.

<Component (H)>

The component (H) is a compound having a structure that decomposes in the presence of acid to generate an acidic group or a hydroxyl group. The component (H) is decomposed by an acid generated from the photoacid generator (D) to generate an acidic group or a hydroxyl group, and thereby becomes soluble in developers. Thus, the use of such a component (H) along with the component (D) permits formation of positive patterns.

The structure that decomposes in the presence of acid to generate an acidic group or a hydroxyl group in the component (H) is the same as the structure that decomposes in the presence of acid to generate an acidic group or a hydroxyl group in the component (A) used in the positive photosensitive composition of the first aspect of the present invention.

In the positive photosensitive composition of the fourth aspect of the present invention, the component (H) may be used alone or in combination of two or more.

The component (D) used in the positive photosensitive composition of the fourth aspect of the present invention is the same as the component (D) used in the positive photosensitive composition of the first aspect of the present invention.

The positive photosensitive composition of the fourth aspect of the present invention may contain a hydrosilylation catalyst.

The hydrosilylation catalyst is the same as the component (C) used in the positive photosensitive composition of the first aspect of the present invention.

<<Optional Components>>

The positive photosensitive compositions of the first to fourth aspects of the present invention may optionally contain, in addition to the above-mentioned essential components, other components.

Examples of these other components include (I) an alkali-soluble component; (J) a compound that contains an alkenyl group and has no structure that decomposes in the presence of acid to generate an acidic group or a hydroxyl group; (K) a sensitizer; a hydrosilylation reaction inhibitor; and a solvent. These components will be described below.

<Component (I)>

The positive photosensitive compositions of the first to fourth aspects of the present invention each preferably further contain (I) an alkali-soluble component to improve the solubility in alkaline developers of the positive photosensitive composition and thereby make the positive photosensitive composition highly sensitive.

Examples of the component (I) include compounds having a structure represented by the formula (X1) or (X2) below, phenol group-containing phenolic resins, carboxyl group-containing acrylic resins, amide resins, and imide resins.

These types of component (I) may be used alone or in combination of two or more.

It should be noted that since the positive photosensitive composition of the fourth aspect of the present invention contains a compound having a structure represented by the formula (X1) or (X2) as an essential component, if the positive photosensitive composition of the fourth aspect of the present invention contains the alkali-soluble component (I), it is an alkali-soluble component other than the compound having a structure represented by the formula (X1) or (X2).

In view of forming a thin film excellent in insulation properties, heat resistance, and solvent resistance after baking, the component (I) is preferably a compound having a structure represented by the formula (X1) or (X2), and more preferably a polysiloxane compound having a structure represented by the formula (X1) or (X2).

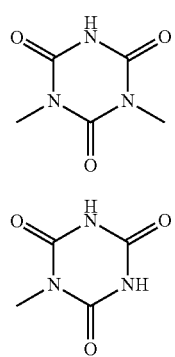

The polysiloxane compound having a structure represented by the formula (X1) or (X2) may be obtained, for example, by a simple method of causing a partial hydrosilylation reaction of a SiH group-containing siloxane compound and a compound containing an alkenyl group and a structure represented by the formula (X1) or (X2). The component (I) prepared by such a method in advance may be used in the positive photosensitive compositions of the first to fourth aspects of the present invention.

Examples of the compounds containing an alkenyl group and a structure represented by the formula (X1) or (X2) include diallyl isocyanuric acid and monoallyl isocyanuric acid. The compound containing an alkenyl group and a structure represented by the formula (X1) or (X2) may also be used in the hydrosilylation reaction for preparing the component (I).

Examples of the SiH group-containing siloxane compounds include the compounds mentioned as the compound having two or more SiH groups within a molecule in the description of the component (A).

If the positive photosensitive composition of the first aspect of the present invention contains the component (I) that is a SiH group- or alkenyl group-containing compound, the component (I) can be used as the component (B) in the positive photosensitive composition of the first aspect of the present invention. Moreover, if the positive photosensitive composition of the first aspect of the present invention contains the component (I) that contains, in addition to a SiH group or an alkenyl group, a structure that decomposes in the presence of acid to generate an acidic group or a hydroxyl group, the component (I) can be used as the component (A) in the positive photosensitive composition of the first aspect of the present invention.

Furthermore, if the positive photosensitive composition of the third aspect of the present invention contains the component (I) that contains a bisphenol structure whose phenolic hydroxyl functional groups are protected by a trialkylsilyl group, the component (I) can be used as the component (F) in the positive photosensitive composition of the third aspect of the present invention.

If the positive photosensitive compositions of the first to fourth aspects of the present invention contains the component (I), the upper limit of the amount of the component (I) is preferably 80 parts by weight, and more preferably 75 parts by weight, per 100 parts by weight of all the components, excluding solvent, in each of the positive photosensitive compositions of the first to fourth aspects of the present invention. Conversely, the lower limit thereof is preferably 15 parts by weight, more preferably 20 parts by weight, and still more preferably 50 parts by weight or more. When the amount of the component (I) falls within the range mentioned above, positive photosensitive compositions excellent in alkaline developability can be provided.

<Component (J)>

The positive photosensitive compositions of the second to fourth aspects of the present invention preferably further contain (J) a compound that contains an alkenyl group and has no structure that decomposes in the presence of acid to generate an acidic group or a hydroxyl group. This is because the use of the component (J) provides improved patterning properties to the positive photosensitive compositions of the first to fourth aspects of the present invention and also provides improved insulation properties and heat resistance to their cured products (thin films).

The component (J) is not particularly limited and may be similar to, for example, the alkenyl group-containing compounds that can be used as the component (B) in the description of the component (B) in the positive photosensitive composition of the first aspect of the present invention.

These types of component (J) may be used alone or in combination of two or more.

If the positive photosensitive composition of the second aspect of the present invention contains the component (J), the amount of the component (J) is preferably 3 to 40 parts by weight, and more preferably 5 to 30 parts by weight, per 100 parts by weight of the component (E).

If the positive photosensitive composition of the third aspect of the present invention contains the component (J), the amount of the component (J) is preferably 3 to 40 parts by weight, and more preferably 5 to 30 parts by weight, per 100 parts by weight of the component (F).

If the positive photosensitive composition of the fourth aspect of the present invention contains the component (J), the amount of the component (J) is preferably 3 to 40 parts by weight, and more preferably 5 to 30 parts by weight, per 100 parts by weight in total of the component (G) and the component (H).

<Component (K)>

The positive photosensitive compositions of the first to fourth aspects of the present invention preferably contain (K) a sensitizer because then they have improved sensitivity to light, especially to short-wavelength light, such as g-line (436 nm), h-line (405 nm), or i-line (365 nm). The component (K) can be used in combination with the component (D) to control curability.

Examples of the component (K) include anthracene compounds and thioxanthone compounds.

In view of a photosensitizing effect, the component (K) is preferably an anthracene compound.

Examples of the anthracene compounds include anthracene, 2-ethyl-9,10-dimethoxy-anthracene, 9,10-dimethyl-anthracene, 9,10-dibutoxy-anthracene, 9,10-dipropoxy-anthracene, 9,10-diethoxy-anthracene, 1,4-dimethoxy-anthracene, 9-methyl-anthracene, 2-ethyl-anthracene, 2-tert-butyl-anthracene, 2,6-di-tert-butyl-anthracene, and 9,10-diphenyl-2,6-di-tert-butyl-anthracene.

Particularly in view of availability, anthracene, 9,10-dimethyl-anthracene, 9,10-dibutoxy-anthracene, 9,10-dipropoxy-anthracene, and 9,10-diethoxy-anthracene are preferred among these.

Moreover, anthracene is preferred in view of providing a cured product excellent in transparency, and 9,10-dibutoxy-anthracene, 9,10-dipropoxy-anthracene, and 9,10-diethoxy-anthracene are preferred in view of providing excellent compatibility with other components.

From the standpoint of storage stability of the positive photosensitive composition, the component (K) is preferably a thioxanthone compound.

Examples of the thioxanthone compounds include thioxanthone, 2-chlorothioxanthone, 2,5-diethylthioxanthone, and isopropylthioxanthone.

In view of availability, 2,5-diethylthioxanthone and isopropylthioxanthone are preferred among these.

These types of component (K) may be used alone or in combination of two or more.

If the positive photosensitive composition of the first aspect of the present invention contains the component (K), the amount of the component (K) is preferably 3 to 50 parts by weight, more preferably 5 to 40 parts by weight, and still more preferably 7 to 35 parts by weight, per 100 parts by weight of the component (A).

If the positive photosensitive composition of the second aspect of the present invention contains the component (K), the amount of the component (K) is preferably 3 to 50 parts by weight, more preferably 5 to 40 parts by weight, and still more preferably 7 to 35 parts by weight, per 100 parts by weight of the component (E).

If the positive photosensitive composition of the third aspect of the present invention contains the component (K), the amount of the component (K) is preferably 3 to 50 parts by weight, more preferably 5 to 40 parts by weight, and still more preferably 7 to 35 parts by weight, per 100 parts by weight of the component (F).

If the positive photosensitive composition of the fourth aspect of the present invention contains the component (K), the amount of the component (K) is preferably 3 to 50 parts by weight, more preferably 5 to 40 parts by weight, and still more preferably 7 to 35 parts by weight, per 100 parts by weight in total of the component (G) and the component (H).

(Hydrosilylation Reaction Inhibitor)

The positive photosensitive compositions of the first to fourth aspects of the present invention may contain a hydrosilylation reaction inhibitor to ensure storage stability.

Examples of the hydrosilylation reaction inhibitors include aliphatic unsaturated bond-containing compounds, organophosphorus compounds, organosulfur compounds, nitrogen-containing compounds, tin compounds, and organic peroxides.

Examples of the aliphatic unsaturated bond-containing compounds include 3-hydroxy-3-methyl-1-butyne, 3-hydroxy-3-phenyl-1-butyne, propargyl alcohols (e.g. 1-ethynyl-1-cyclohexanol), enyne compounds, and maleic acid esters (e.g. dimethyl maleate).

Examples of the organophosphorus compounds include triorganophosphines (e.g. triphenylphosphine), diorganophosphines, organophosphones, and triorganophosphites.

Examples of the organosulfur compounds include organomercaptans, diorganosulfides, hydrogen sulfide, benzothiazole, thiazole, and benzothiazole disulfide.

Examples of the tin compounds include halogenated stannous dihydrates and stannous carboxylates.

Examples of the organic peroxides include di-t-butyl peroxide, dicumyl peroxide, benzoyl peroxide, and t-butyl perbenzoate.

These hydrosilylation reaction inhibitors may be used alone or in combination of two or more.

For good retardation activity and easy availability of raw materials, benzothiazole, thiazole, dimethyl maleate, 3-hydroxy-3-methyl-1-butyne, 1-ethynyl-1-cyclohexanol, and triphenylphosphine are preferred among these hydrosilylation reaction inhibitors.

(Solvent)

The positive photosensitive compositions of the first to fourth aspects of the present invention preferably contain a solvent. By containing a solvent, the positive photosensitive compositions have a reduced viscosity and thus can be uniformly applied when they are cured to form a thin film.

The solvent is not particularly limited, and examples thereof include hydrocarbon solvents such as ethylcyclohexane and trimethylpentane; ether solvents such as 1,4-dioxane and 1,3-dioxolane; ketone solvents such as methyl isobutyl ketone and cyclohexanone; ester solvents such as isobutyl isobutyrate and isobutyl butyrate; glycol solvents such as propylene glycol-1-monomethyl ether-2-acetate (PGMEA), ethylene glycol dimethyl ether, and ethylene glycol diethyl ether; and halogenated solvents such as trifluorotoluene.

These solvents may be used alone or as a solvent mixture containing two or more solvents.

Particularly for easy formation of a uniform film, the solvent is preferably 1,4-dioxane, isobutyl isobutyrate, propylene glycol-1-monomethyl ether-2-acetate, methyl isobutyl ketone, ethylene glycol dimethyl ether, or ethylene glycol diethyl ether.

If the positive photosensitive compositions of the first to fourth aspects of the present invention contain the solvent, the amount of the solvent is not particularly limited and may be appropriately set. The lower limit of the amount of the solvent per 100 parts by weight of the total positive photosensitive composition excluding solvent is preferably 10 parts by weight, more preferably 30 parts by weight, and still more preferably 50 parts by weight. Conversely, the upper limit of the amount thereof is preferably 800 parts by weight, more preferably 400 parts by weight, and still more preferably 300 parts by weight.

Less than 10 parts by weight of the solvent may fail to produce its effects, such as reducing viscosity. Also, more than 800 parts by weight of the solvent may leave residues in the resulting cured product and cause thermal cracks and the like; in addition, such an amount is disadvantageous in cost, reducing the industrial usefulness of the composition.

The positive photosensitive compositions of the first to fourth aspects of the present invention may be prepared by any of various methods. The components may be mixed to prepare the composition immediately before curing, or all the components may previously be mixed to prepare a one-pack solution before it is stored at low temperatures.

The positive photosensitive compositions of the first to fourth aspects of the present invention are materials which can be formed into an insulating film by an application process (coating), and are excellent in electrical contact with the underlying electrode and insulation reliability as mentioned later. Thus, the compositions can be used in thin film transistors as materials satisfying the property requirements for transistors.

The positive photosensitive compositions of the first to fourth aspects of the present invention can be used as materials of the insulating films, such as gate insulator or passivation film, of the thin film transistors of the fifth and sixth aspects of the present invention mentioned below.

<<Thin Film Transistors of Fifth and Sixth Aspects of the Present Invention>>

Next, the thin film transistors of the fifth and sixth aspects of the present invention will be described.

The thin film transistor of the fifth aspect of the present invention includes as a gate insulator a thin film obtained by curing one of the positive photosensitive compositions of the first to fourth aspects of the present invention.

The thin film transistor of the sixth aspect of the present invention includes as a passivation film
a thin film obtained by curing one of the positive photosensitive compositions of the first to fourth aspects of the present invention.

Each of the positive photosensitive compositions of the first to fourth aspects of the present invention may be cured to form a thin film, for example, by a method of coating any type of substrate with the positive photosensitive composition of the first to fourth aspect of the present invention, then exposing the positive photosensitive composition to light through a mask having a desired pattern, and dissolving and removing the exposed portion to form a patterned thin film.

(Photolithography)

The positive photosensitive compositions of the first to fourth aspects of the present invention can be coated on any type of substrate by any method that allows uniform application. Commonly used coating methods may be used, such as spin coating, slit coating, dip coating, roll coating, screen coating, spray coating, spin casting, flow coating, screen printing, ink jet coating, and drop casting.

Depending on the conditions of the particular substrate, the viscosity and the surface tension of the compositions may appropriately be adjusted using a solvent and a surfactant, respectively.

After the coating of the substrate with the positive photosensitive composition of the first to fourth aspect of the present invention, prebaking or a vacuum devolatilization process may be performed prior to the exposure to light, in order to remove the solvent, provided that, since problems such as reduced developability due to heating may occur in this case, the temperature for prebaking is preferably 100° C. or lower, and more preferably 80° C. or lower.

The vacuum devolatilization process and the prebaking may be performed at the same time.

The light source used for exposing the positive photosensitive compositions of the first to fourth aspects of the present invention to light may be a light source that emits light at the absorption wavelength of the photoacid generator (D) or sensitizer (K) used. Typically, light sources having a wavelength in a range from 200 to 450 nm, such as high-pressure mercury lamps, extra-high-pressure mercury lamps, metal halide lamps, high power metal halide lamps, xenon lamps, carbon arc lamps, and light emitting diodes may be used.

Here, the amount of light exposure is not particularly limited, and is preferably 1 to 5000 mJ/cm$^2$, and more preferably 1 to 1000 mJ/cm$^2$.

After the positive photosensitive composition of the first to fourth aspect of the present invention is exposed to light, the composition may be heated. By heating, the unexposed portion is cured to provide a clear contrast.

The temperature for heating is preferably at least 50° C. but not more than 120° C., and is more preferably at least 60° C. but not more than 100° C. for clearer contrast.

After exposing the positive photosensitive composition of the first to fourth aspect of the present invention to light, the exposed portion may be dissolved and removed to form a pattern by any method. Generally used developing methods, such as dipping or spraying may be used.

Here, the developer may be any generally used developer. Specific examples thereof include organic alkaline aqueous solutions such as a tetramethylammonium hydroxide aqueous solution and choline aqueous solution; inorganic alkaline aqueous solutions such as a potassium hydroxide aqueous solution, sodium hydroxide aqueous solution, potassium carbonate aqueous solution, sodium carbonate aqueous solution, and lithium carbonate aqueous solution; mixtures of these aqueous solutions with alcohols, surfactants or the like for adjusting rate of dissolution or the like; and various organic solvents.

(Post-Baking)

After dissolving and removing the exposed portion, post-baking may also be performed to improve the strength and the reliability of the thin film.

The temperature for post-baking is preferably 100° C. to 300° C., and more preferably 150° C. to 250° C.

In the case of using a substrate made of plastic, the temperature for post-baking is preferably as low as possible. The positive photosensitive compositions of the first to fourth aspects of the present invention, which can be post-baked at 150° C. to 200° C., can be post-baked without adversely affecting such a substrate.

In curing the positive photosensitive composition of the first to fourth aspect of the present invention to form a thin film, post-baking may be carried out by heating after dissolving and removing the exposed portion, to allow a curing reaction to proceed to provide a thin film with high insulation properties.

The curing reaction may, for example, be a sol-gel reaction or a hydrosilylation reaction. In view of forming a thin film excellent particularly in insulation properties at lower temperatures, the curing reaction is preferably a hydrosilylation reaction. The hydrosilylation reaction proceeds in the presence of an alkenyl group-containing compound, a SiH group-containing compound, and a hydrosilylation catalyst in the positive photosensitive composition of the first to fourth aspect of the present invention.

In the manner mentioned above, patterned thin films can be formed from the positive photosensitive compositions of the first to fourth aspects of the present invention.
(Insulation Properties)

The thus formed thin films each function as an excellent insulating film.

Insulating films for use in LSIs, TFTs, touch panels or the like are required to have a small leakage current. The thin film having a thickness of 1 μm preferably has a leakage current of not more than 10 nA/cm$^2$, more preferably not more than 5 nA/cm$^2$.
(Thin Film Transistor)

The thin film transistor herein means a thin film field-effect transistor (FET). Specifically, the thin film transistor refers to a three-terminal transistor consisting of source, drain, and gate electrodes, or a four-terminal transistor consisting of source, drain, and gate electrodes and a back gate, that use the electric field of a channel created by applying a voltage to the gate electrode, to control the current between the source and drain.

The thin films obtained by curing the positive photosensitive compositions of the first to fourth aspects of the present invention can be used as a gate insulator for separating the semiconductor layer from the gate electrode, or a passivation film for protecting the semiconductor layer and insulating the source or drain electrode from the pixel electrode in the thin film transistors of the fifth and sixth aspects of the present invention.

The gate insulator in a thin film transistor refers to an insulating film formed between the gate electrode and the semiconductor layer and is a member that requires quite high insulation reliability because even a slight current leakage may cause malfunction of the transistor. The passivation film refers to an insulating film that functions to protect the semiconductor layer, and like the gate insulator, is a member that requires high insulation reliability.

The structures of the thin film transistors of the fifth and sixth aspects of the present invention are described referring to the figures.

FIG. 1 is a schematic cross sectional view illustrating an example of the thin film transistor of the fifth aspect of the present invention. As shown in FIG. 1, a thin film transistor 100 of the fifth aspect of the present invention has a structure in which a substrate (gate electrode) 11, a gate insulator 12 formed of a thin film obtained by curing one of the positive photosensitive compositions of the first to fourth aspects of the present invention, and a semiconductor layer 13 are stacked in this order, and source and drain electrodes 14 and 15 are formed so as to be in contact with both the gate insulator 12 and the semiconductor layer 13.

Figure 2:
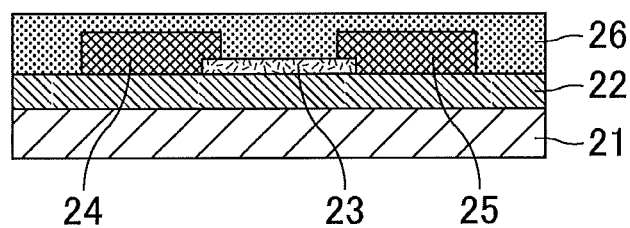
FIG. 2 is a schematic cross sectional view illustrating an example of the thin film transistor of the sixth aspect of the present invention.

FIG. 2 is a schematic cross sectional view illustrating an example of the thin film transistor of the sixth aspect of the present invention. As shown in FIG. 2, a thin film transistor 200 of the sixth aspect of the present invention has a structure in which a substrate (gate electrode) 21, a gate insulator 22, and a semiconductor layer 23 are stacked in this order; source and drain electrodes 24 and 25 are formed so as to be in contact with both the gate insulator 22 and the semiconductor layer 23; and a passivation film 26 formed of a thin film obtained by curing one of the positive photosensitive compositions of the first to fourth aspects of the present invention is further formed so as to cover both the semiconductor layer 23 and the source and drain electrodes 24 and 25.

The structures of the thin film transistors of the fifth and sixth aspects of the present invention are not particularly limited to the structures described above referring to the figures. The thin film transistors may be designed by using various combinations and arrangements according to the display device structure used with the thin film transistor. For example, the gate electrode may be arranged as a bottom gate type or top gate type, and the source and drain electrodes may be arranged as a bottom contact type or top contact type.

The substrate (gate electrode) may be any substrate generally used in the art.

Moreover, examples of the materials for the semiconductor layer include organic semiconductor compounds such as pentacene compounds, oligothiophene compounds, and phthalocyanine compounds; and inorganic semiconductor compounds such as Si compounds, ZnO compounds, and IGZO compounds. Organic semiconductor compounds are preferred among these in that they can be formed into semiconductor layers at low temperatures and thus all the processes can be performed at low temperatures. Moreover, inorganic semiconductor compounds such as Si compounds and ZnO compounds are preferred in that they can be formed into semiconductor layers by a coating process and thus reduction in the take time for the film formation and the like can be expected.

Moreover, the thickness of the semiconductor layer is preferably 10 to 500 nm, regardless of whether the material for the semiconductor layer is an inorganic semiconductor compound or an organic semiconductor compound.

The material for the source/drain electrode is not particularly limited. In view of easy availability, mention may be made of, for example, Au, Al, Pt, Mo, Ti, Cr, Ni, Cu, and ITO; conductive polymers such as PEDOT/PSS; conductive pastes; and metal inks.

Al, Mo, Ti, Cr, Ni, and Cu are preferred among these in that they have low resistance and provide high conductivity; ITO and PEDOT/PSS are preferred in that they can be applied to parts requiring transparency; Au and Pt are preferred in that the surface of the electrode is less likely to be oxidized and thus has excellent stability; and conductive polymers such as PEDOT/PSS, conductive pastes, and metal inks are preferred in that they can be formed into electrodes by a printing process.

The gate insulator and the passivation film may be formed by the methods used to form a thin film by curing one of the positive photosensitive compositions of the first to fourth aspects of the present invention.

The thin film transistors of the fifth and sixth aspects of the present invention may be used as pixel transistors in active-matrix flat panel displays. The important properties of pixel transistors capable of stably driving the displays are threshold voltage, carrier mobility, and on/off current ratio.

The threshold voltage refers to a voltage at which the transistor is switched on and electric current starts flowing in the semiconductor layer. Using a graph of the relationship between $(I_d)^{1/2}$ and $V_g$ ($I_d$ denotes the electric current flowing between the source and drain, and $V_g$ denotes the voltage applied to the gate) of the current transfer characteristics of the transistor, the threshold voltage is calculated from the intersection of an extension of the linear portion and the $V_g$ axis.

The carrier mobility is an important index showing the quality of the TFT device. A higher index indicates that the TFT device serves better as a TFT element. The carrier mobility is preferably 0.5 or higher.

The on/off current ratio is defined as a ratio of maximum current to minimum current ($I_{on}/I_{off}$) of the current $I_d$ flowing between the source and drain of the current transfer characteristics of the transistor. A higher ratio indicates that the transistor functions better as a switch. The on/off current ratio is preferably $10^4$ or more so that even a drive scheme requiring a large current for driving can be applied.

During the use in an actual device, even a transistor failing to satisfy one of the above properties causes a fatal failure. Thus, all the properties need to be satisfied.

Moreover, the element with a high on/off current ratio and a high carrier mobility tends to have higher hysteresis. Thus, the transistor preferably simultaneously has the following properties: a high on/off current ratio, a high carrier mobility, and low hysteresis.

The voltage $V_d$ applied between the source and drain electrodes and the voltage $V_g$ applied to the gate electrode are not particularly limited and may be appropriately set according to the semiconductor material and the drive scheme used. In view of saving the power consumption of the transistor, they are each preferably –50 to 50 V, and more preferably –20 to 20 V.

<<Compound of the Seventh Aspect of the Present Invention>>

The compound of the seventh aspect of the present invention is a compound represented by the following formula (III):

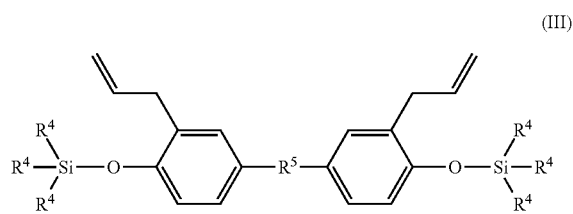

(III)

wherein $R^4$s each represent a $C_{1-6}$ alkyl group having no unsaturated bond, and $R^4$s may be the same as or different from one another; and $R^5$ is any structure that allows the compound to form a bisphenol compound.

Positive photosensitive compositions in which the compound represented by the formula (III) is used show excellent patterning properties and provide excellent electrical insulation reliability.

EXAMPLES

The following is the description of the examples and comparative examples of the present invention. The present invention is not limited to these examples.

The examples and comparative examples were evaluated by the following methods.

(Evaluation for Thin Film Formability and Photolithographic Properties: Patterning Properties)

To a glass substrate (50×50 mm) with a molybdenum thin film having a thickness of 2000 Å, each of the positive photosensitive compositions obtained in Examples 1 to 8 and 11 to 14, and Comparative Examples 1 and 2 mentioned later was applied by spin coating to form a film having a thickness of 1 μm. The film was dried on a hot plate at 70° C. for one minute, and then exposed to light through a photomask having a 20 μm hole pattern with a mask aligner MA-10 (from MIKASA CO., LTD) at 100 mJ/cm², followed by heating at 70° C. for one minute. The resulting film was developed in an alkaline developer (a 2.38% TMAH aqueous solution, from TAMA CHEMICALS CO., LTD.) and then post-baked at 200° C. for 30 minutes, whereby a thin film was formed. The generated pattern was observed with a microscope. A film having a hole pattern is rated good, whereas a film without a hole pattern is rated poor.

(Evaluation of Insulation Properties: Leakage Current)

A thin film was formed on a glass substrate with a molybdenum thin film by the above process. An aluminum electrode (3 mmΦ) was formed on the film with a vacuum evaporator to prepare a capacitor. Then leakage current between the upper and lower electrodes was measured.

(on/Off Current Ratio)

The current $I_{on}$ when switching on is defined as the maximum current in the saturation region of a current transfer characteristic curve, and the current $I_{off}$ when switching off is defined as the minimum current during the off state. An on/off current ratio $I_{on}/I_{off}$ was calculated from the maximum current during the on state and the minimum current during the off state.

(Threshold Voltage)

The threshold voltage $V_{th}$ is defined as the voltage value at the X-intercept of the tangent in the saturation region (gate voltage $V_g$=30 to 40 V) of the current transfer characteristics.

(Carrier Mobility)

A carrier mobility μ was calculated using the following equation with the $I_d$ at a gate voltage $V_g$ of 40 V of the current transfer characteristics.

$$\mu = 2(L \times I_d)/(W \times (\in/d) \times (V_g - V_{th})^2)$$

L: channel length (80 μm)
$I_d$: current between source and drain
W: channel width (2 mm)
$\in$: dielectric constant (2.57E-11)
d: film thickness
$V_g$: gate voltage
$V_{th}$: threshold voltage (Electrical Contact with the Underlying Electrode)

A probe was brought into contact with a throughhole (100 μm×100 μm) formed on the electrode of the thin film transistor by photolithography as described later in Examples 9 and 10, and Comparative Examples 3 and 4. A transistor having electrical contact is rated good, whereas a transistor having no contact with the electrode (a transistor without flow of current) due to residues of the positive photosensitive composition is rated poor.

(Synthesis of Bisphenol S Compound with Protected Functionality)

A 100-mL recovery flask was charged with 20 g of dioxane and 5 g of diallyl bisphenol S, and the mixture was stirred at room temperature. When the mixture became a homogeneous solution, 2.5 g of hexamethyldisilazane was added and the reaction was terminated in two hours. After the solvent and the reaction residues were removed, the presence of the peak derived from trimethylsilyl group and the absence of the peak derived from hydroxyl group were confirmed by $^1$H-NMR. Thus, a diallyl bisphenol S (reactant (1), 6.5 g) whose hydroxyl groups were protected with trimethylsilyl groups was obtained. The chemical formula of the reactant (1) is shown below.

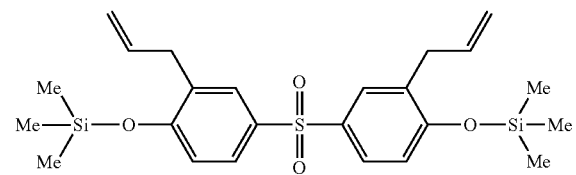 [SMILES: C=CCc1cc(S(=O)(=O)c2ccc(O[Si](C)(C)C)c(CC=C)c2)ccc1O[Si](C)(C)C]

(Synthesis of Bisphenol a Compound with Protected Functionality)

A 100-mL recovery flask was charged with 20 g of dioxane and 5 g of diallyl bisphenol A, and the mixture was stirred at room temperature. When the mixture became a homogeneous solution, 2.5 g of hexamethyldisilazane was added and the reaction was terminated in two hours. After the solvent and the reaction residues were removed, the presence of the peak derived from trimethylsilyl group and the absence of the peak derived from hydroxyl group were confirmed by $^1$H-NMR. Thus, a diallyl bisphenol A (reactant (2), 6.5 g) whose hydroxyl groups were protected with trimethylsilyl groups was obtained. The chemical formula of the reactant (2) is shown below.

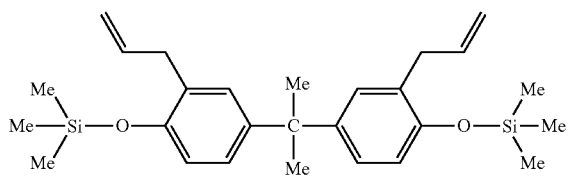 [SMILES: C=CCc1cc(C(C)(C)c2ccc(O[Si](C)(C)C)c(CC=C)c2)ccc1O[Si](C)(C)C]

(Synthesis 2 of Bisphenol S Compound with Protected Functionality)

A 100-mL recovery flask was charged with 20 g of dioxane and 5 g of diallyl bisphenol S, and the mixture was stirred at room temperature. When the mixture became a homogeneous solution, 5 g of di-tert-butyl dicarbonate was added and the reaction was terminated in four hours. After the solvent and the reaction residues were removed, the presence of the peak derived from butoxycarbonyl group and the absence of the peak derived from hydroxyl group were confirmed by $^1$H-NMR. Thus, a diallyl bisphenol S (reactant (3), 6.5 g) whose hydroxyl groups were protected with butoxycarbonyl groups was obtained. The chemical formula of the reactant (3) is shown below.

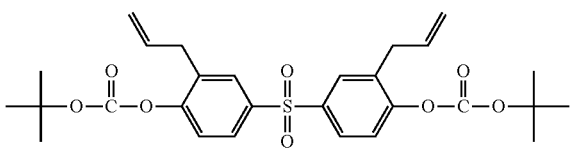 [SMILES: C=CCc1cc(S(=O)(=O)c2ccc(OC(=O)OC(C)(C)C)c(CC=C)c2)ccc1OC(=O)OC(C)(C)C]

Synthesis Example 1

A 100-mL four-neck flask was charged with 20 g of toluene and 3 g of 1,3,5,7-tetramethylcyclotetrasiloxane. The gas phase of the flask was purged with nitrogen and the mixture was then heated to an inner temperature of 100° C. and stirred. A liquid mixture of 5 g of the reactant (1) synthesized by the above process, 0.7 mg of a platinum vinylsiloxane complex in xylene (containing 3% by weight of platinum), and 5 g of toluene was added dropwise to the flask.

After the dropwise addition, the absence of the peak derived from allyl group was confirmed by $^1$H-NMR. Toluene was then evaporated under reduced pressure to give a clear and colorless liquid "reactant A". By $^1$H-NMR measurement, the resulting product was confirmed to be a polysiloxane compound that had a bisphenol S structure protected with trimethylsilyl groups and contained 6.0 mmol/g of SiH groups as determined using dibromoethane as a standard and expressed in equivalents.

Synthesis Example 2

A 100-mL four-neck flask was charged with 20 g of toluene and 3 g of 1,3,5,7-tetramethylcyclotetrasiloxane. The gas phase of the flask was purged with nitrogen and the mixture was then heated to an inner temperature of 100° C. and stirred. A liquid mixture of 5 g of the reactant (1) synthesized by the above process, 0.7 mg of a platinum vinylsiloxane complex in xylene (containing 3% by weight of platinum), and 5 g of toluene was added dropwise to the flask.

After the dropwise addition, the absence of the peak derived from allyl group was confirmed by $^1$H-NMR. The temperature inside the flask was set to 80° C. and 1 g of vinylcyclohexene was added thereto. After the addition, the absence of the peak derived from vinyl group was confirmed by $^1$H-NMR. Toluene was then evaporated under reduced pressure to give a clear and colorless liquid "reactant B". By $^1$H-NMR measurement, the resulting product was confirmed to be a polysiloxane compound that had a bisphenol S structure protected with trimethylsilyl groups and contained 4.0 mmol/g of SiH groups and 2 mmol/g of cyclohexene groups as determined using dibromoethane as a standard and expressed in equivalents.

Synthesis Example 3

A 100-mL four-neck flask was charged with 20 g of toluene and 3 g of 1,3,5,7-tetramethylcyclotetrasiloxane. The gas phase of the flask was purged with nitrogen and the mixture was then heated to an inner temperature of 100° C. and stirred. A liquid mixture of 5 g of the reactant (2) synthesized by the above process, 0.7 mg of a platinum vinylsiloxane complex in xylene (containing 3% by weight of platinum), and 5 g of toluene was added dropwise to the flask.

After the dropwise addition, the absence of the peak derived from allyl group was confirmed by $^1$H-NMR. Toluene was then evaporated under reduced pressure to give a clear and colorless liquid "reactant C". By $^1$H-NMR measurement, the resulting product was confirmed to be a polysiloxane compound that had a bisphenol A structure protected with trimethylsilyl groups and contained 6.0 mmol/g of SiH groups as determined using dibromoethane as a standard and expressed in equivalents.

Synthesis Example 4

A 100-mL four-neck flask was charged with 20 g of toluene and 4 g of 1,3,5,7-tetramethylcyclotetrasiloxane. The gas phase of the flask was purged with nitrogen and the mixture was then heated to an inner temperature of 100° C. and stirred. A liquid mixture of 2 g of the reactant (1) synthesized by the above process, 1 g of monoallyl isocyanuric acid, 2 g of triallyl isocyanurate, 0.7 mg of a platinum vinylsiloxane complex in xylene (containing 3% by weight of platinum), and 5 g of toluene was added dropwise to the flask.

After the dropwise addition, the absence of the peak derived from allyl group was confirmed by $^1$H-NMR. Toluene was then evaporated under reduced pressure to give a clear and colorless liquid "reactant D". By $^1$H-NMR measurement, the resulting product was confirmed to be a polysiloxane compound that had a bisphenol S structure protected with trimethylsilyl groups and contained 3.0 mmol/g of SiH groups as determined using dibromoethane as a standard and expressed in equivalents.

Synthesis Example 5

A 100-mL four-neck flask was charged with 20 g of toluene and 6 g of 1,3,5,7-tetramethylcyclotetrasiloxane. The gas phase of the flask was purged with nitrogen and the mixture was then heated to an inner temperature of 100° C. and stirred. A liquid mixture of 2 g of the reactant (1) synthesized by the above process, 1.5 g of diallyl isocyanuric acid, 1.5 g of triallyl isocyanurate, 0.7 mg of a platinum vinylsiloxane complex in xylene (containing 3% by weight of platinum), and 5 g of toluene was added dropwise to the flask.

After the dropwise addition, the absence of the peak derived from allyl group was confirmed by $^1$H-NMR. The temperature inside the flask was set to 80° C. and 0.5 g of vinylcyclohexene was added thereto. After the addition, the absence of the peak derived from vinyl group was confirmed by $^1$H-NMR. Toluene was then evaporated under reduced pressure to give a clear and colorless liquid "reactant E". By $^1$H-NMR measurement, the resulting product was confirmed to be a polysiloxane compound that had a bisphenol S structure protected with trimethylsilyl groups and contained 1.8 mmol/g of SiH groups and 1 mmol/g of cyclohexene groups as determined using dibromoethane as a standard and expressed in equivalents.

Synthesis Example 6

A 100-mL four-neck flask was charged with 20 g of toluene and 4 g of 1,3,5,7-tetramethylcyclotetrasiloxane. The gas phase of the flask was purged with nitrogen and the mixture was then heated to an inner temperature of 105° C. and stirred. A liquid mixture of 2 g of the reactant (1) synthesized by the above process, 3.7 g of diallyl isocyanuric acid, 6.5 mg of a platinum vinylsiloxane complex in xylene (containing 3% by weight of platinum), and 25 g of dioxane was added dropwise to the flask.

After the dropwise addition, the absence of the peak derived from allyl group was confirmed by $^1$H-NMR. The solvent was then evaporated under reduced pressure to give a clear and colorless liquid "reactant F". By $^1$H-NMR measurement, the resulting product was confirmed to be a polysiloxane compound that had a bisphenol S structure protected with trimethylsilyl groups and contained 3.2 mmol/g of SiH groups as determined using dibromoethane as a standard and expressed in equivalents.

Comparative Synthesis Example 1

A 500-mL four-neck flask was charged with 100 g of toluene and 20 g of 1,3,5,7-tetramethylcyclotetrasiloxane. The gas phase of the flask was purged with nitrogen and the mixture was then heated to an inner temperature of 105° C. and stirred. A liquid mixture of 10 g of bisphenol S diallyl ether, 0.0017 g of a platinum vinylsiloxane complex in xylene (containing 3% by weight of platinum), and 10 g of toluene was added dropwise to the flask.

After the dropwise addition, the absence of the peak derived from allyl group was confirmed by $^1$H-NMR and the reaction was terminated. Toluene was then evaporated under reduced pressure to give a clear and colorless liquid "reactant G". By $^1$H-NMR measurement, the resulting product was confirmed to be a polysiloxane compound that contained 4.0 mmol/g of SiH groups as determined using dibromoethane as a standard and expressed in equivalents.

Comparative Synthesis Example 2

A 500-mL four-neck flask was charged with 100 g of toluene and 36 g of 1,3,5,7-tetramethylcyclotetrasiloxane. The gas phase of the flask was purged with nitrogen and the mixture was then heated to an inner temperature of 105° C. and stirred. A liquid mixture of 5 g of triallyl isocyanurate, 0.0039 g of a platinum vinylsiloxane complex in xylene (containing 3% by weight of platinum), and 10 g of toluene was added dropwise to the flask.

After the dropwise addition, the absence of the peak derived from allyl group was confirmed by $^1$H-NMR and the reaction was terminated. Toluene was then evaporated under reduced pressure to give a clear and colorless liquid "reactant H". By $^1$H-NMR measurement, the resulting product was confirmed to be a polysiloxane compound that contained 9.0 mmol/g of SiH groups as determined using dibromoethane as a standard and expressed in equivalents.

Examples 1 to 8, Comparative Examples 1 and 2

Positive photosensitive compositions were prepared by blending the reactants A to H obtained in Synthesis Examples 1 to 6 and Comparative Synthesis Examples 1 and 2, the reactant (1) synthesized by the above process, an iodonium salt photoacid generator (BBI-103, from Midori Kagaku Co., Ltd.), a sulfonium salt photoacid generator (DTS-103, from Midori Kagaku Co., Ltd.), a sensitizer (K) (trade name: DBA, dibutoxy-anthracene, from Kawasaki Kasei Chemicals Ltd.), D4V (1,3,5,7-tetravinyl-1,3,5,7-tetramethylcyclotetrasiloxane), TAIC (triallyl isocyanurate), and a solvent (isobutyl isobutyrate) in the weight ratios shown in Table 1. The obtained positive photosensitive compositions were evaluated for patterning properties and leakage current by the methods mentioned above. The results are shown in Table 2.

TABLE 1

|  |  |  | Example | | | | | | | | Comparative Example | |
|---|---|---|---|---|---|---|---|---|---|---|---|---|
|  |  |  | 1 | 2 | 3 | 4 | 5 | 6 | 7 | 8 | 1 | 2 |
| Synthesis | 1 | Reactant A | 0.8 |  |  |  |  | 0.5 | 0.6 | 0.8 |  |  |
| Example | 2 | Reactant B |  | 0.6 |  |  |  |  |  |  |  |  |
|  | 3 | Reactant C |  |  | 0.8 |  |  |  |  |  |  |  |
|  | 4 | Reactant D |  |  |  | 0.8 |  |  |  |  |  |  |
|  | 5 | Reactant E |  |  |  |  | 0.6 |  |  |  |  |  |
|  | 6 | Reactant F |  | 0.2 |  |  |  |  | 0.2 |  |  |  |

TABLE 1-continued

|  |  | Example |  |  |  |  |  |  |  | Comparative Example |  |
|---|---|---|---|---|---|---|---|---|---|---|---|
|  |  | 1 | 2 | 3 | 4 | 5 | 6 | 7 | 8 | 1 | 2 |
| Comparative Synthesis Example | 1 Reactant G | | | | | | | | | 0.8 | |
|  | 2 Reactant H | | | | | | | | | | 0.8 |
|  | Reactant (1) | | | | | | 0.5 | | | | |
|  | D4V | 0.2 | | 0.2 | | | | | 0.2 | | |
|  | TAIC | | | | 0.2 | 0.2 | | 0.2 | | 0.2 | 0.6 |
| (D) Photoacid generator | BBI-103 | 0.02 | 0.016 | 0.02 | 0.02 | 0.02 | 0.02 | 0.02 | | 0.02 | |
|  | DTS-103 | | | | | | | | 0.02 | | |
| (K) Sensitizer | DBA | 0.02 | 0.016 | 0.02 | 0.02 | 0.02 | 0.02 | 0.02 | 0.02 | 0.02 | |
| Solvent | Isobutyl isobutyrate | 3 | 2.4 | 3 | 3 | 3 | 3 | 3 | 3 | 3 | 3.3 |

TABLE 2

|  | Example |  |  |  |  |  |  |  | Comparative Example |  |
|---|---|---|---|---|---|---|---|---|---|---|
|  | 1 | 2 | 3 | 4 | 5 | 6 | 7 | 8 | 1 | 2 |
| Patterning properties | Good | Good | Good | Good | Good | Good | Good | Good | Poor | Poor |
| Leakage current (nA/cm$^2$) | 2 | 3 | 3 | 3 | 3 | 1 | 2 | 2 | 12 | 2 |

The results shown in Table 2 indicate that the positive photosensitive compositions of the present invention have better patterning properties than the compositions of the comparative examples, and the thin films obtained by curing the positive photosensitive compositions of the present invention have better insulation properties than the thin films obtained by curing the compositions of the comparative examples.

Example 9, Comparative Example 3

A gate electrode was prepared using a p-type highly doped Si substrate as a conductive layer. The positive photosensitive composition obtained in Example 1 or Comparative Example 2 was applied to the gate electrode by spin coating at 1000 rpm for 30 sec., dried on a hot plate at 70° C. for one minute, and then exposed to light through a photomask having a 100 μm hole pattern with a mask aligner MA-10 (from MIKASA CO., LTD) at 100 mJ/cm$^2$, followed by heating at 70° C. for one minute. Then the product was developed in an alkaline developer (a 2.38% TMAH aqueous solution, from TAMA CHEMICALS CO., LTD.) to form a contact hole, followed by post-baking at 180° C. for one hour, whereby a gate insulator was formed.

Further, an IGZO oxide semiconductor layer having a thickness of 500 Å was formed using a sputtering apparatus (SENTRON, from SHIMADZU EMIT CO., LTD.) at a pressure of 1.0 Pa under 40 sccm of Ar and 5 sccm of O$_2$. On the IGZO oxide semiconductor layer, Ti source/drain electrodes each having a thickness of 300 Å were formed by evaporation through a mask having a channel length of 80 μm and a channel width of 2 mm. Thus, a thin film transistor was prepared.

Example 10, Comparative Example 4

A gate electrode with a gate insulator was prepared using as a conductive layer a p-type highly doped Si substrate with a 3000 Å-thick thermal oxide layer. An IGZO oxide semiconductor layer and Ti source/drain electrodes were formed thereon in the same manner as in Example 9 and Comparative Example 3. Further, a passivation film was formed from the positive photosensitive composition obtained in Example 1 or Comparative Example 2 by the same procedure as used to form a gate insulator in Example 9 and Comparative Example 3. Thus, a thin film transistor was prepared.

The current transfer characteristics of the thin film transistors prepared in Examples 9 and 10 and Comparative Examples 3 and 4 were evaluated with a semiconductor parameter analyzer (Agilent 4156). Based on the current transfer characteristics of the thin film transistors, on/off current ratios, threshold voltages, and carrier mobilities of the thin film transistors were calculated by the methods mentioned earlier. Also, the gate insulators and passivation films formed from the positive photosensitive compositions were evaluated for electrical contact with the underlying electrode. The results are shown in Table 3.

TABLE 3

|  | Example 9 | Example 10 | Comparative Example 3 | Comparative Example 4 |
|---|---|---|---|---|
| Positive photosensitive composition | Example 1 | Example 1 | Comparative Example 2 | Comparative Example 2 |
| Post-baking temperature | 180° C. | 180° C. | 180° C. | 180° C. |
| On/off current ratio | $1.5 \times 10^5$ | $3.4 \times 10^5$ | $1.2 \times 10^5$ | $1.8 \times 10^5$ |
| Threshold voltage (V) | −18 | −14 | −18 | −15 |
| Carrier mobility (cm$^2$/Vs) | 1 | 1.1 | 0.9 | 1 |
| Electrical contact with the underlying electrode | Good | Good | Poor | Poor |

The results shown in Table 3 indicate that the thin film transistors including as a gate insulator or a passivation film a thin film obtained by curing a positive photosensitive composition of the present invention simultaneously have a high on/off ratio and a high carrier mobility and, at the same time, exhibit excellent electrical contact with the underlying electrode.

Synthesis Example 7

A 100-mL four-neck flask was charged with 20 g of toluene and 5 g of the reactant (1) synthesized by the above process. The gas phase of the flask was purged with nitrogen and the mixture was heated to an inner temperature of 100° C. and stirred. A liquid mixture of 0.5 g of tetraallyloxyethane and 5 g of toluene was added dropwise to the flask.

After the dropwise addition, the absence of the peak derived from allyl group was confirmed by $^1$H-NMR. Toluene was then evaporated under reduced pressure to give a clear and colorless liquid "reactant I". By $^1$H-NMR measurement, the resulting product was confirmed to be a polysiloxane compound that contained 2.9 mmol/g of SiH groups and 0.4 mmol/g of acetal bonds as determined using dibromoethane as a standard and expressed in equivalents (corresponding to the component (G)).

Synthesis Example 8

A 100-mL four-neck flask was charged with 20 g of toluene and 3 g of 1,3,5,7-tetramethylcyclotetrasiloxane. The gas phase of the flask was purged with nitrogen and the mixture was heated to an inner temperature of 100° C. and stirred. A liquid mixture of 5 g of 1,3-adamantanediol diacrylate, 0.7 mg of a platinum vinylsiloxane complex in xylene (containing 3% by weight of platinum), and 5 g of toluene was added dropwise to the flask.

After the dropwise addition, the absence of the peak derived from allyl group was confirmed by $^1$H-NMR. Toluene was then evaporated under reduced pressure to give a clear and colorless liquid "reactant J". By $^1$H-NMR measurement, the resulting product was confirmed to be a polysiloxane compound that contained 4.5 mmol/g of SiH groups as determined using dibromoethane as a standard and expressed in equivalents.

(Synthesis of Compound Having Polyhedral Polysiloxane Structure)

To 1262 g of a 48% choline aqueous solution (trimethyl-2-hydroxyethyl-ammonium hydroxide aqueous solution) was added 1083 g of tetraethoxysilane, and the mixture was vigorously stirred at room temperature for two hours. When the reaction system generated heat and became a homogeneous solution, the stirring was slowed down and the reaction was further continued for 12 hours. To the solids formed in the reaction system was then added 1000 mL of methanol to prepare a homogeneous solution.

The methanol solution was slowly added dropwise to a solution of 716 g of dimethylvinylchlorosilane, 516 g of trimethylsilyl chloride, and 1942 mL of hexane under vigorous stirring. After completion of the dropwise addition, the mixture was reacted for one hour and then the organic layer was extracted and condensed to give solids. The formed solids were washed by vigorous stirring in methanol and then filtered to obtain tetrakis(vinyldimethylsiloxy)-tetrakis(trimethylsiloxy)octasilsesquioxane (reactant (4), 601 g) which is a compound having a polyhedral polysiloxane structure containing 16 Si atoms and 4 vinyl groups.

Synthesis Example 9

A 300-mL four-neck flask was charged with 52.8 g of toluene and 18 g of 1,3,5,7-tetramethylcyclotetrasiloxane. The gas phase of the flask was purged with nitrogen and the mixture was heated to an inner temperature of 105° C. and stirred. A liquid mixture of 7.5 g of the reactant (4) synthesized by the above process, 7.5 g of diallyl isocyanurate, 6 mg of a platinum vinylsiloxane complex in xylene (containing 3% by weight of platinum), 45 g of dioxane, and 15 g of toluene was added dropwise to the flask.

After the dropwise addition, the absence of the peak derived from allyl group was confirmed by $^1$H-NMR. Dioxane and toluene were then evaporated under reduced pressure to give a clear and colorless liquid "reactant K". The reactant K was confirmed to contain a SiH group by $^1$H-NMR. The reactant K was a compound corresponding to the component (B) and an alkali-soluble component and had a polyhedral polysiloxane structure. By $^1$H-NMR measurement, the reactant K was confirmed to be a compound that contained 4.3 mmol/g of SiH groups as determined using p-xylene as a standard and expressed in equivalents.

Synthesis Example 10

A 300-mL four-neck flask was charged with 52.8 g of toluene and 18 g of 1,3,5,7-tetramethylcyclotetrasiloxane. The gas phase of the flask was purged with nitrogen and the mixture was heated to an inner temperature of 105° C. and stirred. A liquid mixture of 12 g of diallyl isocyanurate, 6 mg of a platinum vinylsiloxane complex in xylene (containing 3% by weight of platinum), 45 g of dioxane, and 15 g of toluene was added dropwise to the flask.

After the dropwise addition, the absence of the peak derived from allyl group was confirmed by $^1$H-NMR. Dioxane and toluene were then evaporated under reduced pressure to give a clear and colorless liquid "reactant L". The reactant L was confirmed to contain a SiH group by $^1$H-NMR. The reactant L was a compound corresponding to the component (B) and an alkali-soluble component. By $^1$H-NMR measurement, the reactant L was confirmed to be a compound that contained 3.8 mmol/g of SiH groups as determined using p-xylene as a standard and expressed in equivalents.

Examples 11 to 15

Positive photosensitive compositions were prepared by blending the reactants A, F, and I to L obtained in Synthesis Examples 1 and 6 to 10, the reactants (1) and (3) synthesized by the above processes, a sulfonium salt photoacid generator (DTS-103, from Midori Kagaku Co., Ltd.), a sensitizer (K) (trade name: DBA, dibutoxy-anthracene, from Kawasaki Kasei Chemicals Ltd.), TAIC (triallyl isocyanurate), and a solvent (isobutyl isobutyrate) in the weight ratios shown in Table 4. The obtained positive photosensitive compositions were evaluated for patterning properties and leakage current by the methods mentioned earlier. The results are shown in Table 5.

TABLE 4

| | | | Example | | | | |
|---|---|---|---|---|---|---|---|
| | | | 11 | 12 | 13 | 14 | 15 |
| Synthesis | 1 | Reactant A | | | | | 0.5 |
| Example | 6 | Reactant F | | | | 0.5 | |
| | 7 | Reactant I | 0.8 | | | | |
| | 8 | Reactant J | | 0.8 | | | |

TABLE 4-continued

| | | 11 | 12 | 13 | 14 | 15 |
|---|---|---|---|---|---|---|
| 9 | Reactant K | | | 0.5 | | |
| 10 | Reactant L | | | | | 0.3 |
| | Reactant (1) | | | 0.5 | | |
| | Reactant (3) | | | | 0.5 | |
| | TAIC | 0.2 | 0.2 | | | 0.2 |
| (D) Photoacid generator | DTS-103 | 0.02 | 0.02 | 0.02 | 0.02 | 0.02 |
| (K) Sensitizer | DBA | 0.02 | 0.02 | 0.02 | 0.02 | 0.02 |
| Solvent | Isobutyl isobutyrate | 3 | 3 | 3 | 3 | 3 |

TABLE 5

| | Example | | | | |
|---|---|---|---|---|---|
| | 11 | 12 | 13 | 14 | 15 |
| Patterning properties | Good | Good | Good | Good | Good |
| Leakage current (nA/cm$^2$) | 2 | 3 | 3 | 3 | 2 |

REFERENCE SIGNS LIST

100, 200: Thin film transistor
11, 21: Substrate (gate electrode)
12, 22: Gate insulator
13, 23: Semiconductor layer
14, 15, 24, 25: Source/drain electrode
26: Passivation film

The invention claimed is:

1. A positive photosensitive composition, comprising:
   (A) a compound that contains an alkenyl group or a SiH group within a molecule and has a structure that decomposes in the presence of acid to generate an acidic group or a hydroxyl group;
   (B) a compound that contains a SiH group or an alkenyl group within a molecule;
   (C) a hydrosilylation catalyst; and
   (D) a photoacid generator.

2. The positive photosensitive composition according to claim 1,
   wherein the component (B) is a compound having no structure that decomposes in the presence of acid to generate an acidic group or a hydroxyl group.

3. The positive photosensitive composition according to claim 1,
   wherein the component (A) is a compound that contains a SiH group within a molecule and has a structure that decomposes in the presence of acid to generate an acidic group or a hydroxyl group, and the component (B) is a compound that contains an alkenyl group within a molecule.

4. The positive photosensitive composition according to claim 1,
   wherein the structure that decomposes in the presence of acid to generate an acidic group or a hydroxyl group in the component (A) is a phenol structure with protected functionality or a carboxylic acid structure with protected functionality.

5. The positive photosensitive composition according to claim 4,
   wherein the phenol structure with protected functionality is a bisphenol structure with protected functionality.

6. The positive photosensitive composition according to claim 5,
   wherein the bisphenol structure with protected functionality is a bisphenol structure whose functionality is protected by a trialkylsilyl group or a butoxycarbonyl group.

7. The positive photosensitive composition according to claim 5,
   wherein the bisphenol structure is a bisphenol S structure or a bisphenol F structure.

8. The positive photosensitive composition according to claim 4,
   wherein the carboxylic acid structure with protected functionality contains an acetal bond or a carboxylic acid tertiary ester bond.

9. The positive photosensitive composition according to claim 8,
   wherein the structure containing a carboxylic acid tertiary ester bond is protected by an aliphatic ring structure.

10. The positive photosensitive composition according to claim 9,
    wherein the aliphatic ring structure is an adamantane structure.

11. The positive photosensitive composition according to claim 1,
    wherein at least one of the component (A) and the component (B) is a siloxane-based compound.

12. The positive photosensitive composition according to claim 11,
    wherein of the components (A) and (B), at least the component (A) is a siloxane-based compound, and the component (A) has a cyclic siloxane structure.

13. The positive photosensitive composition according to claim 11,
    wherein the siloxane-based compound contains a polyhedral polysiloxane structure formed of 6 to 24 Si atoms.

14. The positive photosensitive composition according to claim 13,
    wherein the polyhedral polysiloxane structure is obtained by a hydrosilylation reaction of a SiH group-containing siloxane compound and an alkenyl group-containing polyhedral polysiloxane compound formed of 6 to 24 Si atoms.

15. The positive photosensitive composition according to claim 13,
    wherein the polyhedral polysiloxane structure is obtained by a hydrosilylation reaction of a polyhedral polysiloxane compound represented by formula (I) and a cyclic siloxane compound represented by formula (II), the formulas (I) and (II) respectively being:

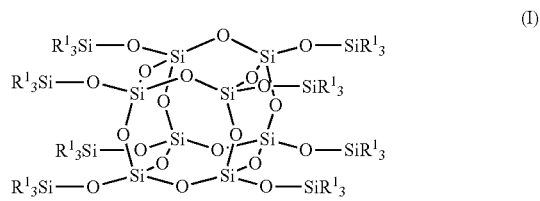

wherein $R^1$s are each a hydrogen atom or a $C_{1-10}$ organic group, at least one of $R^1$s is a hydrogen atom or an alkenyl group, and $R^1$s may be the same as or different from one another, and

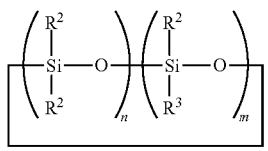
(II)

wherein R²s are each a $C_{1-6}$ organic group and may be the same as or different from one another; R³s are each a hydrogen atom or an alkenyl group and may be the same as or different from one another; n represents an integer of 0 to 10; and m represents an integer of 1 to 10.

16. The positive photosensitive composition according to claim 1,
wherein the component (A) is a compound that decomposes in the presence of acid to become alkali-soluble.

17. A positive photosensitive composition according to claim 1, comprising as the component (A) and the component (B),
(E) a compound obtained by a hydrosilylation reaction of the component (A) and the component (B).

18. The positive photosensitive composition according to claim 1,
wherein the component (D) is an iodonium salt or a sulfonium salt.

19. The positive photosensitive composition according to claim 1, further comprising
(I) an alkali-soluble component.

20. The positive photosensitive composition according to claim 19,
wherein the component (I) is a SiH group- or alkenyl group-containing compound.

21. The positive photosensitive composition according to claim 19,
wherein the component (I) is a compound having a structure represented by the following formula (X1) or (X2):

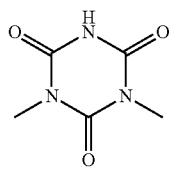
(X1)

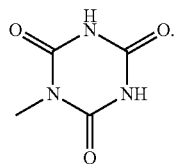
(X2)

22. The positive photosensitive composition according to claim 17, further comprising
(J) a compound that contains an alkenyl group and has no structure that decomposes in the presence of acid to generate an acidic group or a hydroxyl group.

23. The positive photosensitive composition according to claim 1, further comprising
(K) a sensitizer.

24. A thin film transistor, comprising as a gate insulator a thin film obtained by curing the positive photosensitive composition according to claim 1.

25. A thin film transistor, comprising as a passivation film a thin film obtained by curing the positive photosensitive composition according to claim 1.

26. The positive photosensitive composition according to claim 1,
wherein the component (B) is a compound having a structure represented by the following formula (X1) or (X2):

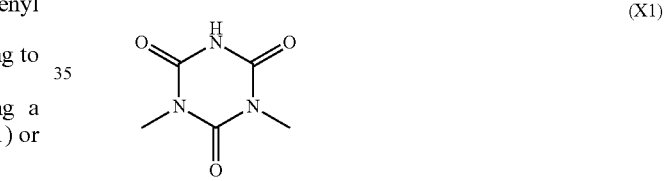
(X1)

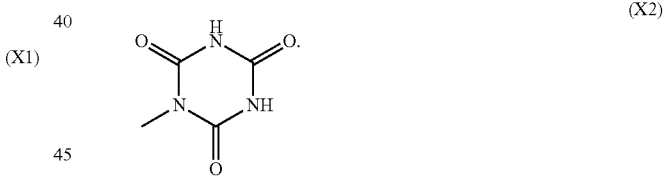
(X2)

* * * * *